US006842244B2

(12) United States Patent
Bédard et al.

(10) Patent No.: US 6,842,244 B2
(45) Date of Patent: Jan. 11, 2005

(54) PARTICLE QUANTIFYING APPARATUS AND METHOD

(75) Inventors: Pierre Bédard, Charlesbourg (CA); Jean-Pierre Couturier, Sainte-Foy (CA); Jean-Guy Boucher, St. Étienne (CA); Jean T. Bédard, Charlesbourg (CA)

(73) Assignee: Centre de Recherche Industrielle du Québec, Montréal (CA)

( * ) Notice: Subject to any disclaimer, the term of this patent is extended or adjusted under 35 U.S.C. 154(b) by 150 days.

(21) Appl. No.: 10/352,132

(22) Filed: Jan. 28, 2003

(65) Prior Publication Data

US 2003/0142310 A1 Jul. 31, 2003

(30) Foreign Application Priority Data

Jan. 29, 2002 (CA) .............................................. 2369802

(51) Int. Cl.[7] .............................................. G01N 21/00
(52) U.S. Cl. ..................................................... 356/338
(58) Field of Search ................................ 356/335–343; 250/573–577; 382/141, 133, 134

(56) References Cited

U.S. PATENT DOCUMENTS

| | | | | |
|---|---|---|---|---|
| 3,787,122 A | * | 1/1974 | Lepper, Jr. ................... | 356/338 |
| 4,001,595 A | * | 1/1977 | Reisman ...................... | 250/575 |
| 4,898,037 A | | 2/1990 | Allen et al. | |
| 4,905,500 A | | 3/1990 | Mason | |
| 5,579,107 A | * | 11/1996 | Wright et al. ................ | 356/336 |
| 6,690,520 B1 | * | 2/2004 | Kusuzawa ................... | 359/740 |

* cited by examiner

Primary Examiner—Michael P. Stafira
(74) Attorney, Agent, or Firm—Jean-Claude Boudreau

(57) ABSTRACT

An apparatus for estimating the quantity of particles collected by a suction extractor includes a capturing element handling assembly including a pair of stationary plates disposed in a spaced relationship to define a gap therebetween, the stationary elements being provided with sets of main apertures disposed in alignment with each other to define a corresponding set of channels extending through the gap. A movable disk interposed within the gap is provided with a plurality of holders capable of receiving a plurality of filter-type particle capturing elements. An actuator operatively coupled to the movable disk provides controlled movement thereof relative to the stationary plates. One of the main apertures on the first stationary plate defines a first inlet in fluid communication with an output fluid carrying line, while one aligned aperture on the second stationary plate defines a first outlet for fluid communication with the output fluid carrying line. The apparatus further includes an optical sensing device disposed in alignment with a secondary aperture provided on the first stationary element and extending therethrough to communicate with the gap, for inspecting a selected particle capturing element to generate a measurement signal representative of optical characteristics of the captured particles, and a data processor for analyzing the measurement signal to generate an estimation of the quantity of particles captured by the selected element. A controller is operatively connected to the actuator to selectively displace the movable disk from a capturing position to an inspection position in respect of a selected particle capturing element. There is provided a device for cleaning a previously inspected capturing element while the selected capturing element is in the capturing position.

23 Claims, 15 Drawing Sheets

FIG_2

FIG_3

FIG_4

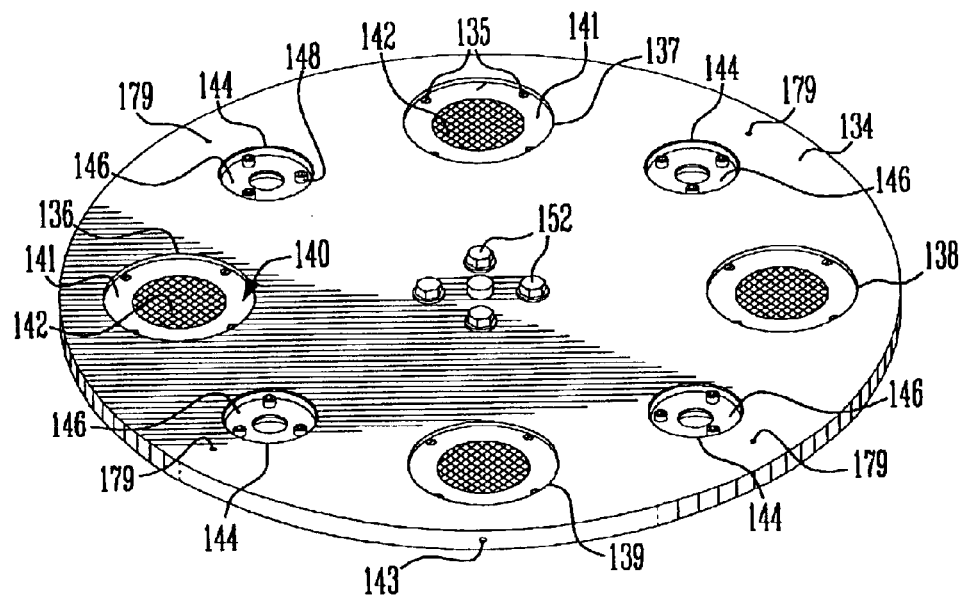
FIG_7A
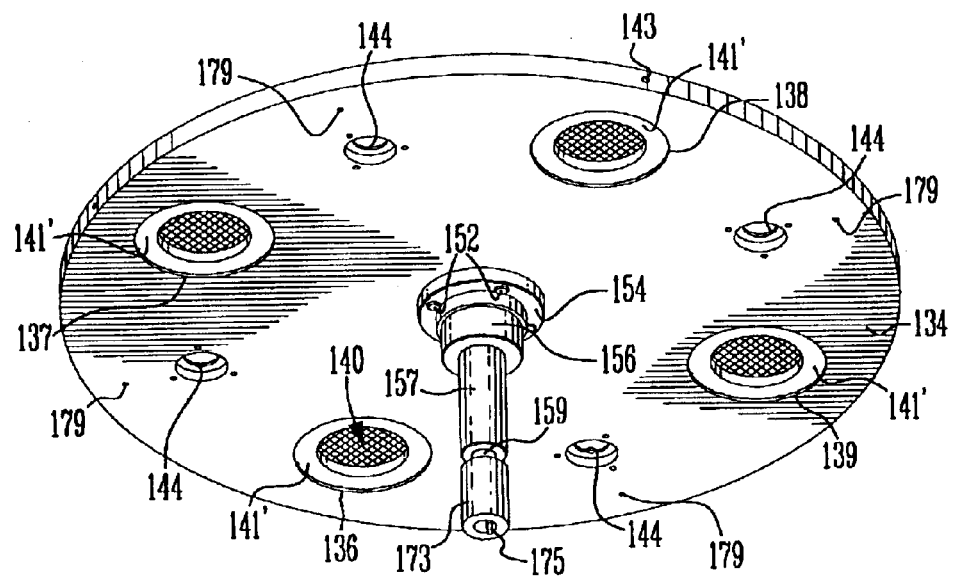
FIG_7B

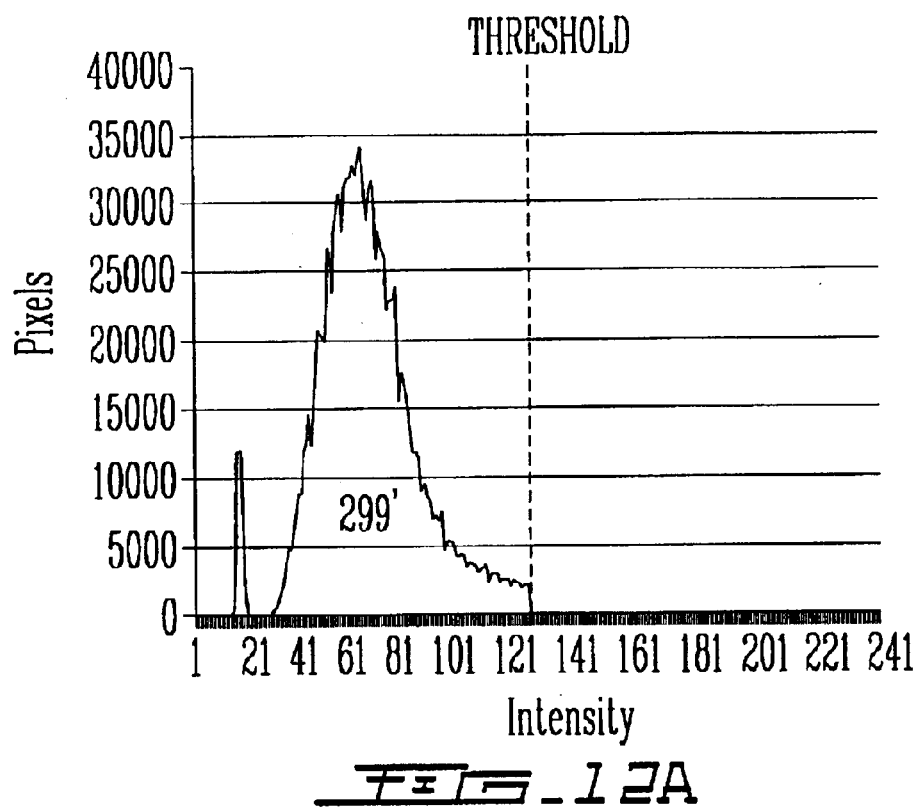
FIG_12A
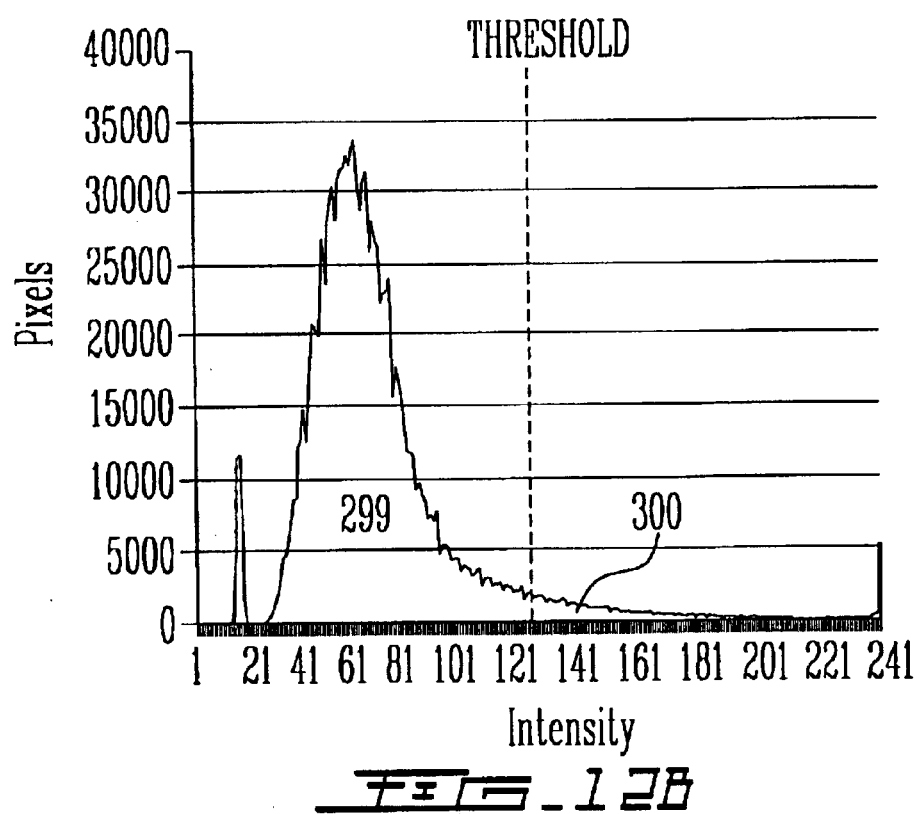
FIG_12B

PARTICLE QUANTIFYING APPARATUS AND METHOD

BACKGROUND OF THE INVENTION

1. Field of the Invention

The present invention relates to the field of measurement instrumentation, and more particularly to automated particle quantifying apparatus and method that can provide estimation of the quantity of particles present in a volume or on a surface, such as particles collected from the surface of a moving web by a suction extractor.

2. Description of the Related Art

In the past years, new measurement instrumentation aimed at detecting and quantifying particle found within or onto a variety of media has been continuously developed either to better comply with the requirements of specific applications or to increase processing speed as often required by real-time industrial applications. Among those industrial fields that have experienced significant instrumentation development is the paper manufacturing industry, for the purpose of detecting and quantifying the small particles that form onto both surfaces of a paper web during manufacturing and due to partial or total fiber separation from the paper web material. This phenomena, commonly known as "linting", involves particles that are generally known to consist of loose and weakly bound fibers originating from ray cells, shives and other fine matter present on the surface of the paper, characterized by a relatively low specific area which does not provide sufficient bounding to the well-adhered fibers constituting the paper web. Although linting generally does not imply significant modification of physical properties of the paper material, it is known to be at the origin of important problems at the subsequent printing process due to lint fiber separation that occurs when the paper is passing through printing equipment. More specifically, during the printing process, the particle or lint material adheres to the printing blanket and interferes with ink transfer thereto, thereby causing gradual dogging of the printing machines while reducing printing quality. Printing interruption that is rendered necessary to perform cleaning or printing machinery contributes to significantly reduce the efficiency of the printing process while increasing printing cost. In an attempt to comply with paper quality requirements from the printing industry which imposes limited levels of linting, the paper manufacturing industry has proposed some techniques to detect and quantify linting on the production site so as to adjust the parameters of pulp and paper production processes accordingly, which parameters relate to raw wood chips blend from resinous and hardwood species, pulp characteristics and processing steps such as sieving and purification steps as well as paper manufacturing machine types.

A known technique for linting measurement consists of using a small commercial printing press installed at the paper-manufacturing location and operated under controlled conditions representative of normal production printing conditions. Following a predetermined operation period, lint particles are collected from the ink train and blanket of the printing press and are then weighed after drying to provide an estimation of the paper's linting propensity. Such off-line technique being expensive and time-consuming, it has been held impracticable to be used as a routine quality control operation.

A known online paper web surface cleaner-tester is disclosed in U.S. Pat. No. 4,905,500 issued to Mason, by which lint material is freed from the surface of a paper web traveling pass a material pickup head having an air bearing surface through and along which an air stream is passed creating a negative pressure causing the air bearing surface to be held in close proximity to the web while causing lint material to be freed from the web surface and carried in the air stream. The material pick-up head uses a vacuum at its inlet opening located relative to the air-bearing surface such that the freed material is sucked into the inlet and transported toward a particle-collecting filter provided with a device for measuring the pressure drop across the filter to determine a preset amount of material captured. The time required to capture the preset amount of material is measured to provide an indication of the paper's linting propensity. Alternatively, the pressure drop after a preset time maybe measured to provide an equivalent estimation. Although representing an improvement over the known off-line technique using a small printing press, the on-line paper web surface cleaner-tester as taught by Mason cannot allow linting measurement on a continuous basis since the filter must be manually changed after being loaded with particles following a single test. Although the predetermined pressure drop value can be set so as to limit the entire particle capturing time to less than one minute, the time required to manually substitute a loaded filter with a new, particle-free filter for performing a following test could hardly be restrained within a reasonable limit so as to provide reliable and useful continuous linting estimation.

In an attempt to improve the measurement rate of paper's linting propensity, an automated dust measuring apparatus has been proposed by Allen et al in U.S. Pat. No. 4,898,037 which uses a cylindrical roll provided with an elastomeric covering adjacent a metal feed cylinder to form a nip through paper sheets are conveyed, whereby dust released from the surface of the paper sheets in contact with the elastomeric covering surface is transferred thereto. The apparatus comprises an electrical drive motor for rotating the cylindrical roll at a predetermined speed and a mechanism to bring the roll at a working position wherein a predetermined pressure is applied to the paper sheets between the roll and the feed cylinder. When one revolution of the roll has been completed, the mechanism is operated to disengage the roll for opening the nip. The apparatus further includes an optical sensing device having a light source and a detector with its associated electronics for measuring the change in reflectance of the elastomeric covering surface of the roll. The elastomeric covering surface is conveniently colored black, for changing to a greyish tone with a buildup of dust. A computer is provided to control the apparatus and to compare the reflectance measurement signal with a previously obtained value for the reflectivity of the clean roll surface considered as a reference. The roll positioning mechanism is preferably a rotary mechanism capable of moving the roll between a dust transferring position wherein it forms with the adjacent feed cylinder a nip contacting the paper sheet passing there between, to a roll cleaning position wherein dust adhered to the surface elastromeric covering is being dislodged through the action of water or cleaning fluid that is circulated into an out of a bath provided at the cleaning position. Disposed at an intermediate position is a hot air blower arranged to blow hot air onto the roll to remove cleaning fluid remaining thereon. Apart from the risk of paper damage due to contact thereof with the roll and feed cylinder at the transfer nip, such automated apparatus cannot allow dust measurement while the capturing roll is brought to the cleaning position and then after to the drying position, thereby significantly limiting dust quantifying rate.

It is therefor still desirable to provide automated apparatus and method for efficiently estimating the quantity of particles collected by a suction extractor and more particularly for estimating the quantity of particles on the surface of a web such as paper web traveling through a collecting area, which advantageously obviate the above-mentioned limitations suffered by known prior art techniques.

BRIEF SUMMARY OF THE INVENTION

It is therefor a main object of the present invention to provide apparatus and method for estimating the quantity of particles collected by a suction extractor which exhibit high measuring rate as required by on-line particle quantifying applications.

According the above main object, from a broad of the present invention, there is provided an apparatus for estimating the quantity of particles collected by a suction extractor through an output fluid carrying line provided thereon. The apparatus comprises a capturing element handling assembly including first and second stationary elements disposed in a spaced relationship to define a gap there between, said stationary elements being provided with respective sets of main apertures disposed in alignment with each other to define a corresponding set of channels extending through the gap, a movable element interposed within the gap and being provided with a plurality of holders capable of receiving a plurality of filter-type particle capturing elements, and an actuator operatively coupled to the movable element for providing controlled movement of the movable element relative to the stationary elements, wherein one said main aperture of the first stationary element defines a first inlet in fluid communication with the output fluid carrying line and one corresponding said aligned main aperture on the second stationary element defines a first outlet for fluid communication with the output fluid carrying line through a corresponding said channel. The apparatus further comprises an optical sensing device disposed in alignment with a secondary aperture provided on the first stationary element and extending therethrough to communicate with the gap, for inspecting a selected one of said particle capturing element to generate a measurement signal representative of optical characteristics of the collected particles as captured by the selected element. The apparatus also comprises a data processor for analyzing said measurement signal to generate an estimation of the quantity of particles captured by the selected element; and
a controller operatively connected to the actuator to selectively displace the movable element from a first position wherein one of said two holders is aligned with the first inlet and outlet so that correspondingly received said particle capturing element captures the particles during a first predetermined period of time, to a second position where said one holder having the selected capturing element received therein is aligned with the secondary aperture so as to be inspected upon operation of the optical sensing device.

In accordance with the same above main object, from a further broad aspect of the invention, there is provided an apparatus for estimating the quantity of particles on at least a first surface of a web traveling through a collecting area. The apparatus comprises an air suction extractor including a first particle collecting head having an air intake disposed within the collecting area in close proximity to the first web surface and coupled to an output air carrying line connected to an air suction source to convey collected particles through said output line, a capturing element handling assembly including first and second stationary elements disposed in a spaced relationship to define a gap there between, said stationary elements being provided with respective sets of main apertures disposed in alignment with each other to define a corresponding set of channels extending through the gap, a movable element interposed within the gap and being provided with a plurality of holders capable of receiving a plurality of filter-type particle capturing elements, and an actuator operatively coupled to the movable element for providing controlled movement of the movable element relative to the stationary elements, wherein one said main aperture of the first stationary element defines a first inlet in fluid communication with the output fluid carrying line and one corresponding said aligned main aperture on the second stationary element defines a first outlet for fluid communication with the output fluid carrying line through a corresponding said channel. The apparatus further comprises an optical sensing device disposed in alignment with a secondary aperture provided on the first stationary element and extending therethrough to communicate with the gap, for inspecting a selected one of said particle capturing element to generate a measurement signal representative of optical characteristics of the collected particles as captured by the selected element. The apparatus also comprises a data processor for analyzing the measurement signal to generate an estimation of the quantity of particles captured by the selected element, and a controller operatively connected to the actuator for selectively displace the movable element from a first position wherein one of said two holders is aligned with the first inlet and outlet so that correspondingly received said particle capturing element captures the particles during a first predetermined period of time, to a second position where said one holder having the selected capturing element received therein is aligned with the secondary aperture so as to be inspected upon operation of the optical sensing device.

According to the same above main object, from a still further broad aspect of the invention, there is provided a method for estimating the quantity of particles collected by a, suction extractor through an output fluid carrying line provided thereon, comprising the steps of: i) interposing a first filter-type particle capturing element within said output fluid carrying line during a predetermined period of time to capture a corresponding quantity of said collected particles; ii) inspecting the particle-capturing element with an optical sensor to generate a measurement signal representative of optical characteristics of the collected particles as captured by the element; iii) analyzing the measurement signal to generate an estimation of the quantity of particles captured by the element; iv) circulating a cleaning fluid through the first particle capturing element in a direction so as to remove said quantity of collected particles; and simultaneously to said step iv): v) interposing a further filter-type particle capturing element within said output fluid carrying line during a further said first predetermined period of time to capture a corresponding further quantity of said collected particles; vi) repeating said steps ii) and iii) with the further particle capturing element.

In accordance with the same above main object of the invention, from a still further broad aspect thereof, there is provided a method for estimating the quantity of particles on at least a first surface of a web traveling through a collecting area, comprising the steps of: i) applying suction within the collecting area in close proximity to the first web surface to collect said particles and convey thereof through an output air carrying line; ii) interposing a first filter-type particle-capturing element within the output fluid carrying line during a predetermined period of time to capture a corresponding quantity of said collected particles; iii) inspecting the first particle-capturing element with an optical sensor to generate a measurement signal representative of optical characteristics of the collected particles as captured by the element; iv) analyzing said measurement signal to generate an estimation of the quantity of particles captured by the element: v) circulating a cleaning fluid through the first particle capturing element in a direction so as to remove said quantity of collected particles; and simultaneously to said step v): vi) interposing a further filter-type particle capturing element within the output fluid carrying line during a further said first predetermined period of time to capture a corresponding further quantity of said collected particles; vii) repeating said steps iii) and iv) with the further particle capturing element.

BRIEF DESCRIPTION OF THE DRAWINGS

Preferred embodiments of apparatus and method for estimating the quantity of particles as collected by a suction extractor according to the invention will now be described in detail with the accompanying drawings in which:

FIG. 7a is a three-dimensional top view of a movable plate as part of the handling assembly provided on the apparatus of FIG. 3;

FIG. 7b is a three-dimensional bottom view of the movable plate of FIG. 7a;

FIG. 12a is a graph representing a histogram obtained from an inspected particle-free capturing element image used as a reference for image analyzing purpose;

FIG. 12b is a graph representing a histogram obtained from a particle-loaded capturing element image for analysis in combination with the histogram of FIG. 12a;

DETAILED DESCRIPTION OF THE PREFERRED EMBODIMENTS

In the following description, preferred embodiments of the particle quantifying apparatus and method according to the invention will now be explained in detail in the context of a paper manufacturing process wherein a paper web is traveling at high speed between working nips of a paper making system, for providing an evaluation of the paper web's linting propensity. However, it is to be understood that paper material in other form than web, such as sheets, can be subjected to measurement provided by the same apparatus and method described below, when used with appropriate handling devices that may be readily designed by any one skilled in the mechanical art. Moreover, it is more generally contemplated to adapt the apparatus and method according to the invention to any application requiring the quantification of particles as collected by a suction extractor, either collected from the surface of any object or contained in suspension within a liquid or gas filling a given volume.

Figure 1:
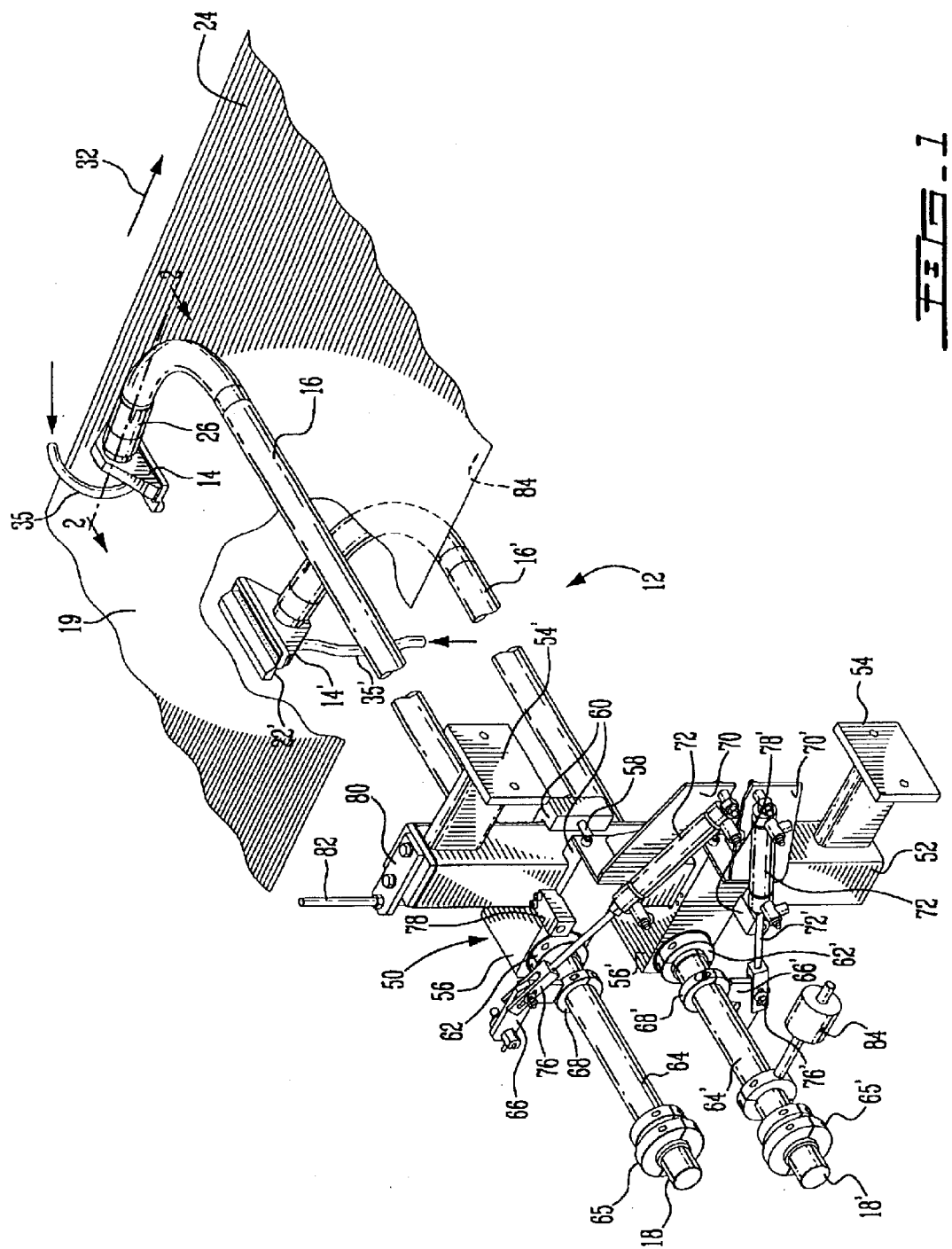
FIG. 1 is a three-dimensional view of an air suction particle extractor that can be used as part or with a first preferred embodiment of the apparatus according to the invention, in the context of a paper web linting measurement application.

Referring now to FIG. 1, a particle suction extractor as generally designated at 12 for use or as part of an apparatus according to the invention includes a first particle collecting head 14 connected to an output air carrying line in the form a first rigid conduit 16 for conveying collected particles through an output end 18 provided on conduit 16 by the action of a downstream suction source that will be described later in detail with reference to FIGS. 3–5. Such particle collecting head 14 can be obtained from Leading Edge Applications, Surrey B.C., Canada.

Figure 2:
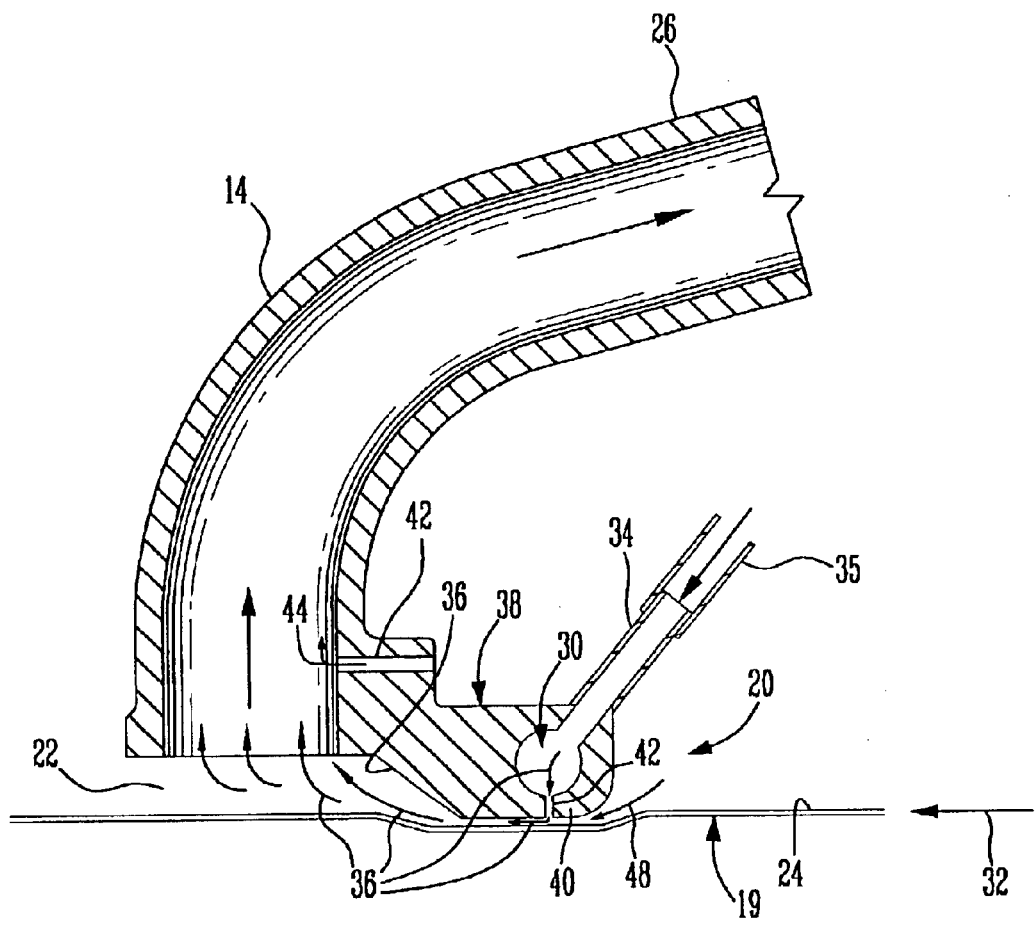
FIG. 2 is a schematic cross sectional rear side view along lines 2—2 of FIG. 1 showing internal details of the first particle collecting head.

Turning now to FIG. 2 representing the first particle collecting head viewed in cross-section, a paper web 19 is shown while it is traversing a particle collecting area generally designated at 20 wherein the particle collecting head 14 is located using a positioning device that will be later described in detail with reference to FIG. 1. As shown in FIG. 2, the collecting head 14 has an air intake 22 disposed within the collecting area 20 in close proximity to the first web surface 24 and coupled to the output air carrying conduit through a tubular outlet 26 adapted to fit thereto. The particle collecting head 14 further has an air injector generally designated at 30 disposed upstream of air intake 22 in the traveling direction of the web 19 as indicated by arrow 32 and is connected through an air inlet 34 through a supply conduit 35 as also shown in FIG. 1, to a forced air source that will be later explained in more detail with reference to FIGS.

3–5, for feeding an airflow from inlet 34 as indicated by arrow 35 toward intake 22 as indicated by arrows 36 to dislodge and convey loose and weakly bound particles present on the surface 24 of web 19 as it is traveling through the inspection area adjacent collecting head 14 as can be seen on FIG. 2. The injector 30 is part of a head body 38 having an air bearing portion 40 traversed by a plurality of holes 42 as part of injector 30 to uniformly distribute the injected air over the scanned portion of web surface 24 as it passes along the air bearing portion 40. The head body 38 is preferably provided with apertures 42 allowing additional air to enter downstream of air intake 22 toward tubular outlet 26 in the direction of arrow 44, which additional flow of air tends to direct the airflow indicated by arrows 36 away from intermediary surface 36 defined by body 38 to prevent accumulation of dislodged particles thereon. As can be seen on FIG. 2, additional air upstream the air bearing portion 40 as indicated by arrow 48 is allowed to further feed the particle dislodging and carrying airflow toward air intake 22 thereby further increasing collecting efficiency. Further detail regarding the design of particle collecting head 14 may be found in U.S. Pat. No. 4,905,500 issued to Mason, the entire specification thereof being incorporated herein by reference.

Referring back to FIG. 1, the conduit 16 and head 14 assembly is preferably mounted on an adjustable holder generally designated at 50 that includes a main support beam 52 that can be conveniently secured to the frame of an adjacent portion of the paper machine through attaching plates 54, 54'. The main support beam 52 is adapted to receive a first mounting block 56 provided with an adjustment assembly including a bolt 58 extending through opposed L-shape portions 60, which bolt 58 can be tightened whenever the mounting block 56 is displaced along main support beam 62 at the desired vertical position therealong. The first rigid conduit 16 is pivotally mounted on the block 56 through a rotary bearing assembly 62 traversed by a base portion 64 of first rigid conduit 16 which is in turn rigidly attached to a lever member 66 with a collar assembly 68. The mounting block 56 is further provided with a supporting flange 70 that pivotally connects a base portion of a first cylinder 72 having its piston rod 74 pivotally connected to lever member 66 through a fork joint 76 having a slot for allowing free floating of the particle capturing head 14 when brought in the working position as shown in FIG. 1. The mounting block 56 is also provided with a stop 78 for limiting the rotating range of the bearing assembly 62 by providing abutment with lever member 66 corresponding to an extractor head storage position. A guiding assembly for the mounting block 56 is also provided which includes a holding plate 80 having a main portion rigidly secured to the upper end of main support beam 52 and a free end portion for receiving a threaded guiding rod 82 downwardly extending through a corresponding bore (not shown) provided on the mounting block 56. In order to allow particle extraction from a bottom surface 84 of web 19, the suction extractor 12 is preferably provided with a second particle collecting head 14' disposed within the collecting area in opposed space relationship with first particle collecting head 14 and having an air intake 22' in close proximity to second bottom surface 84 of web 19 opposed to first top web surface 24, and coupled to the output air carrying line through rigid conduit 16' for conveying collected particles therethrough. As will be later explained in more detail with reference to FIGS. 4 and 5, first and second rigid conduits 16, 16' may be conveniently coupled to a same output air carrying line. It can be seen from FIG. 1 that the second rigid conduit 16' is mounted to the main support beam 52 using a mounting block 56' which is a mirror symmetrical version of mounting block 56 to provide similar vertical and rotational position adjustment of second particle collecting head 14' adjacent bottom surface 84 of web 19. Accordingly, a rotary bearing assembly 62' is also provided on mounting block 56' to receive base portion 64' of second rigid conduit 16' which is in turn rigidly attached to a corresponding lever member 66' through a collar assembly 68'. So as to provide appropriate coupling of conduit base portion 64, which is caused to rotate, with corresponding first conduit output end 18 to be coupled to the output air carrying line, a rotary coupling member 65 is provided to allow relative movement between conduit base portion 64 and conduit output end 18. Similarly, the mounting block 56' is provided with a supporting flange 70' which is pivotally connected to the base portion of a second cylinder 72' having its piston rod 74' pivotally connected to lever member 66' through slotted fork joint 76'. The mounting block 56' is also provided with a stop 78' to limit the rotary movement of the second rigid conduit 16' accordingly. The mounting block 56' also receives a portion of a guiding rod 82 for a vertical displacement relative thereto. The second conduit base portion 64' is similarly coupled to responding second conduit output end 18' with a rotary coupling member 65'. So as to provide a biasing torque on the underneath particle collecting head 14', the second conduit base portion 64' is further rigidly connected to a counterweight device 84 that can be adjusted so that the second particle connected head 14' may be held in an appropriate floating position adjacent the bottom web surface 84 in a similar way as explained above with respect to FIG. 2.

Figure 3:
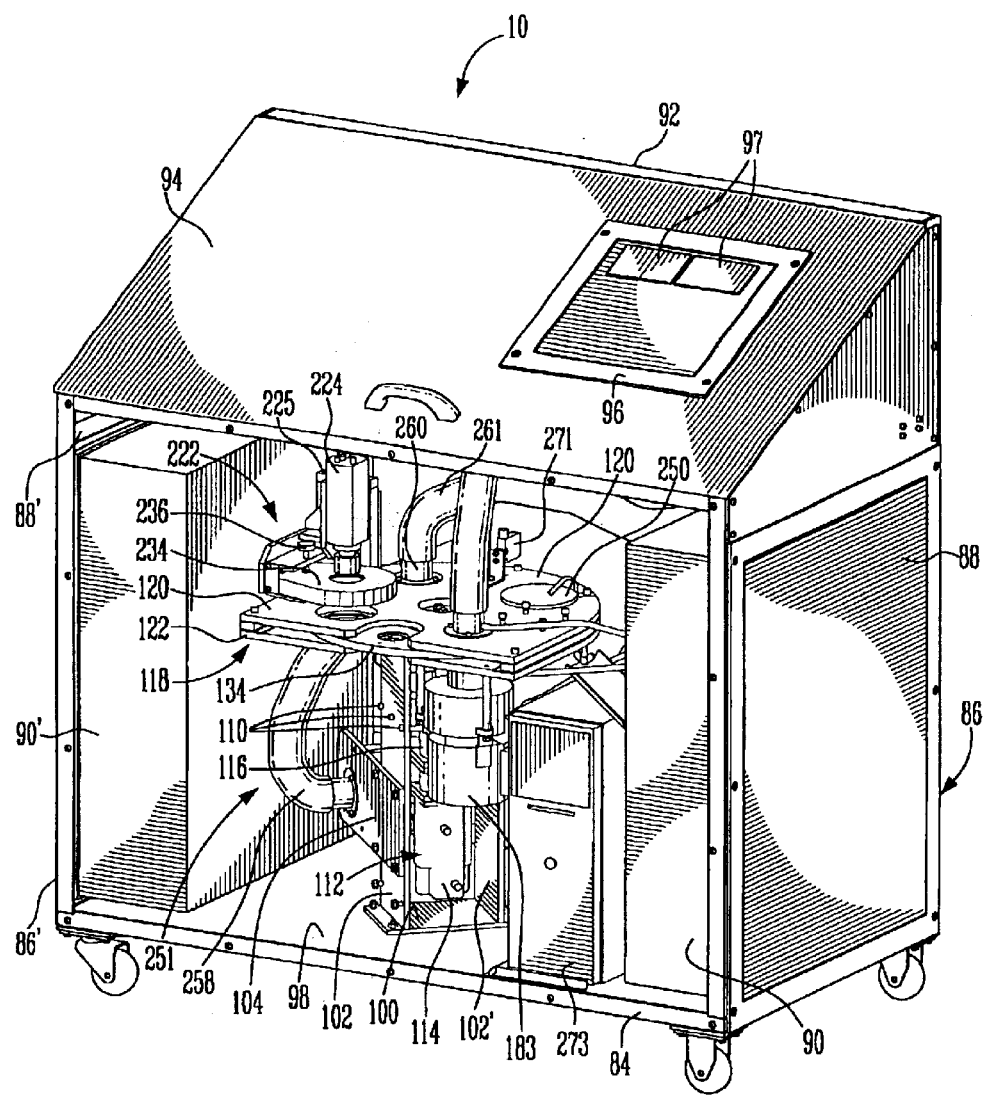
FIG. 3 is a three-dimensional view of the complete particle quantifying apparatus of the first embodiment for use with the particle suction extractor shown in FIG. 1, illustrated with its front side panel removed to show main components of the apparatus.
Figure 6A:
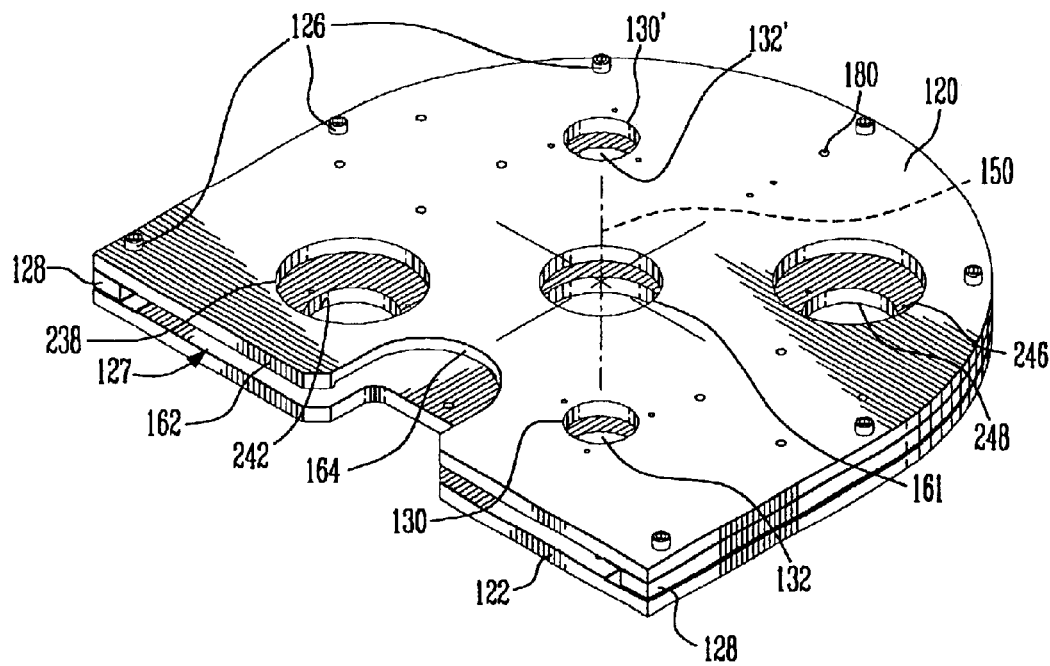
FIG. 6a is a three-dimensional top view of a first stationary plate of the handling assembly provided on the apparatus of FIG. 3.
Figure 6B:
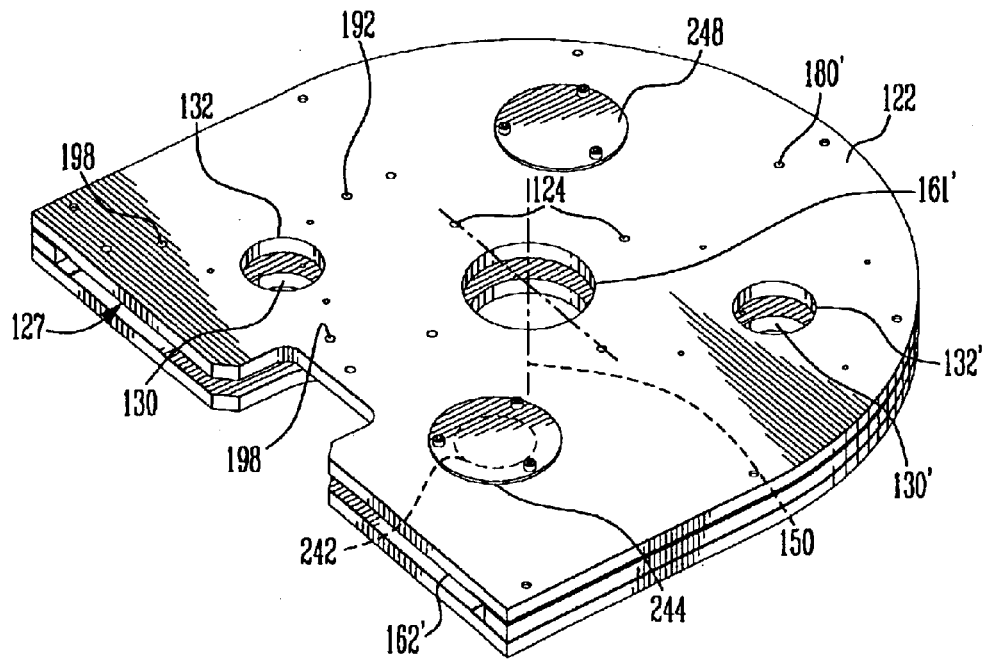
FIG. 6b is a three-dimensional bottom view of a bottom second stationary plate provided on the handling assembly of the apparatus of FIG. 3.
Figure 8:
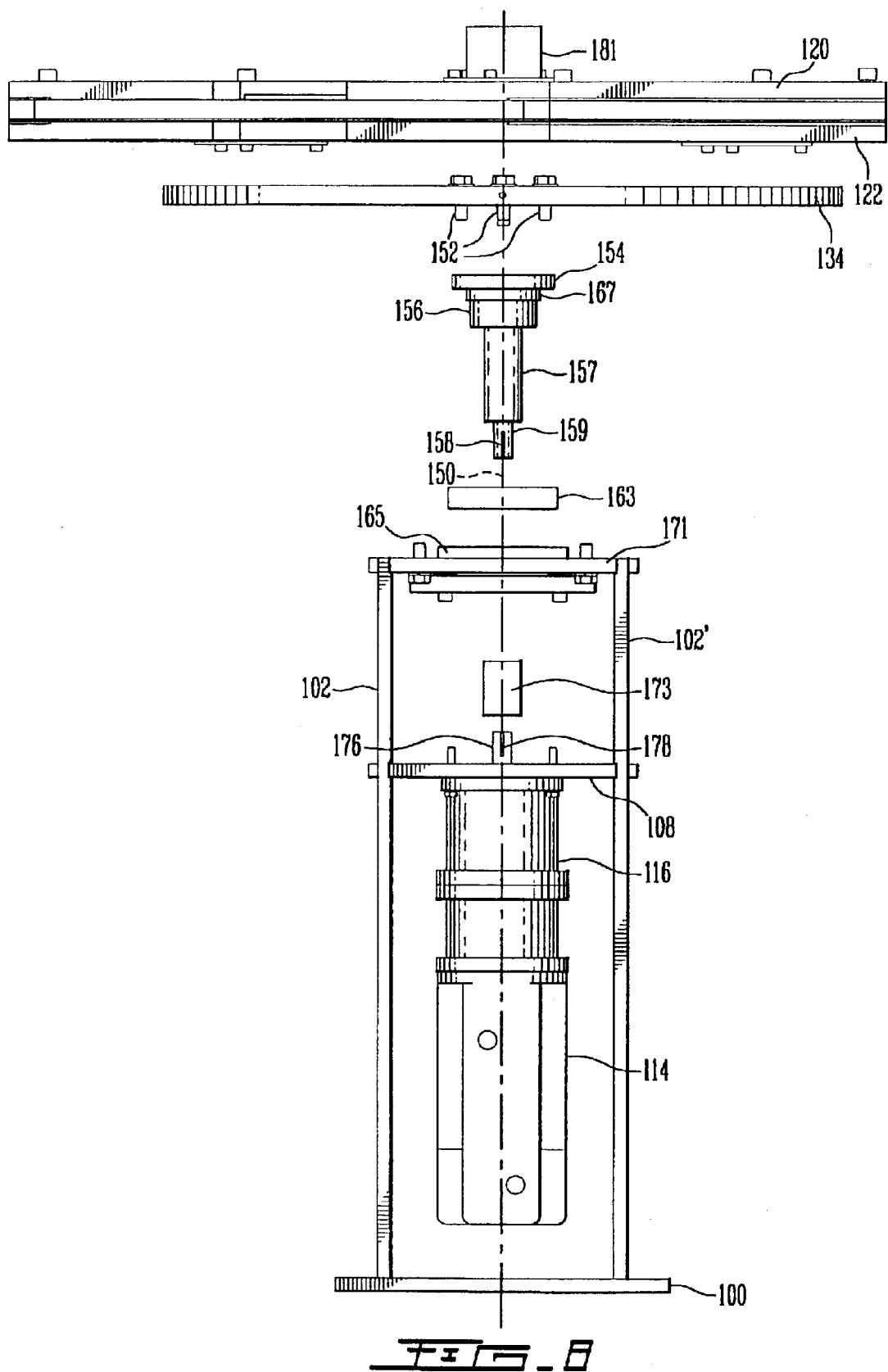
FIG. 8 is a partially exploded side view of a portion of the handling assembly provided on the embodiment of FIG. 3.
Figure 9:
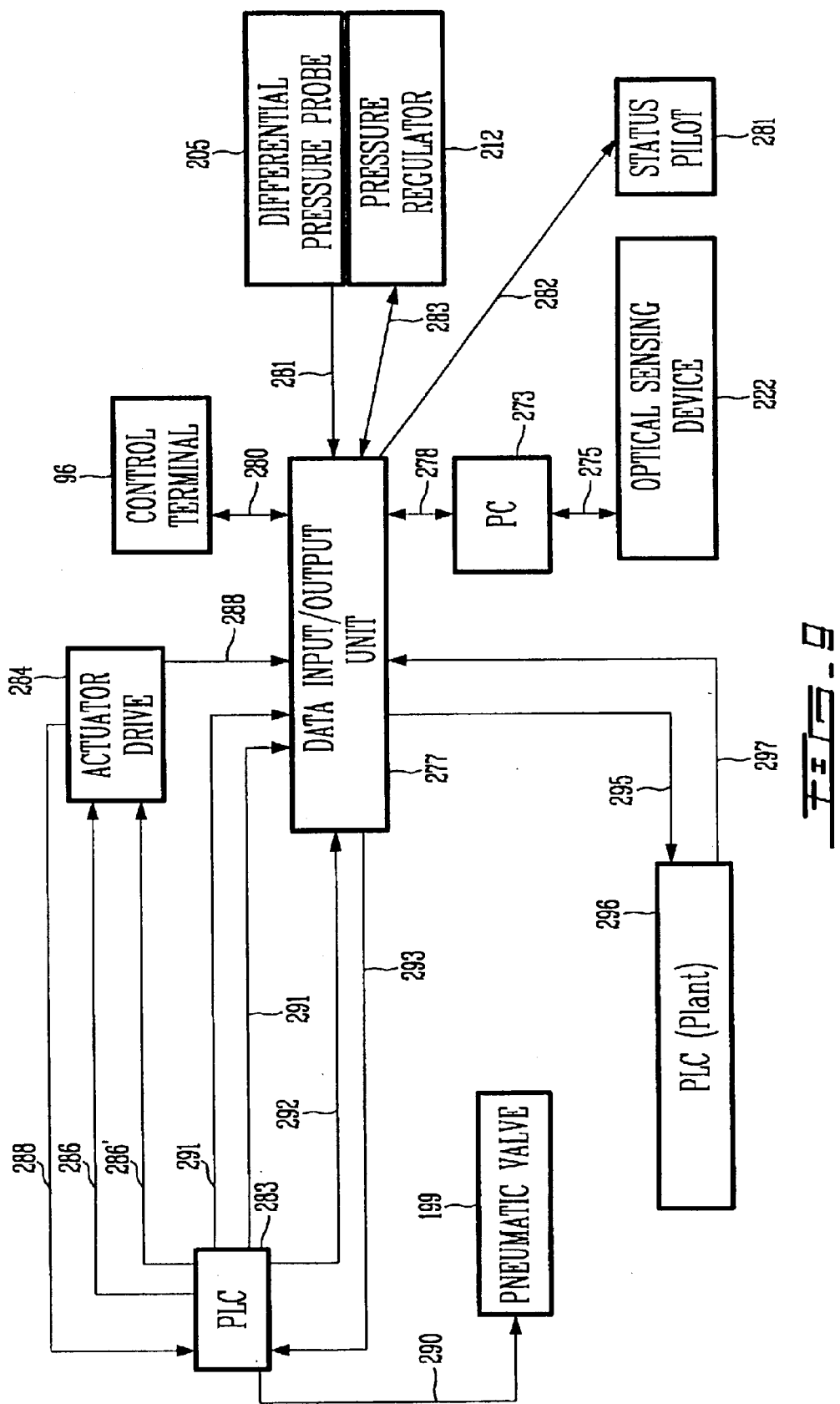
FIG. 9 is a general block diagram of the apparatus of FIG. 3 showing electrical/electronic interconnection between the various control and processing components.

Referring now to FIG. 3, the particle quantifying apparatus according to a preferred embodiment of the invention as generally designated at 10 for use with the suction extractor as described above in view of FIGS. 1 and 2 includes a main frame 84 receiving at opposed ends 86, 86' thereof side panels 88, 88' to which are secured a pair of enclosures 90, 90' for containing electrical and electronic components as part of the apparatus control and data processing subsystem that will be later described in detail with reference to FIG. 9. Pivotally secured to the frame 84 through hinge 92 is a top panel 94 receiving a control terminal 96 the function of which will be explained later with reference to FIGS. 8 and 9. Rigidly secured to a bottom panel 98 provided on frame 84 is a support base 100 having vertically standing side plates 102, 102', to which side plate 102 is rigidly attached a transverse holding plate 104 for securing a vacuum air blower 106 such as model no. 117728-00 from Ametek, as shown in FIG. 4, in which plate 104 has been intentionally shown to illustrate further detail of vacuum air blower 106. As better shown in FIG. 4, the support base 100 is also provided with a horizontal holding plate 108 transversally secured to side plates 102, 102' with bolts 110, to which plate 108 is rigidly held an actuator generally designated at 112 as better shown in FIG. 3. The actuator includes an electrical servo-motor 114 coupled to a speed reducer 116. The actuator 112 is preferably a rotary actuator used to provide controlled movement of the movable disk 134 relative to stationary plates 120, 122 in a manner that will be explained later in detail. In the embodiment shown, a servomotor model N-3412 from Allan Bradley with a 20-1 gear ratio reducer were used. The actuator 112 is part of a handling assembly generally designated at 118 that includes first and second stationary elements in the form of plates 120, 122 secured to a top portion 171 of support base 100 using bolts (not shown) engaging the threaded holes 124 provided on second stationary plate 122 as shown in FIG. 6b. As better shown in FIG. 6a, first and second stationary plates 120, 122 are secured on each other with bolt assemblies 126 while being maintained in a spaced relationship to define a gap there between indicated at 127 using spacers 128 through which both assemblies 126 extend. As shown in FIGS. 6a and 6b, the stationary plates 120, 122 are provided with respective sets of main apertures 130, 130' and 132, 132' respectively, disposed in alignment with each other to define a corresponding set of channels extending through the gap 127.

Turning back to FIG. 3, the handling assembly 118 further includes a movable element in the form a plate or disk 134 which is interposed within the gap and extends in parallel relationship between first and second stationary plates 120, 122. As better shown in FIG. 7a, the movable disk 134 is provided with a plurality of holders 137, 138, 139 capable of receiving a plurality of filter-type particle capturing elements generally designated at 140 using set screws (not shown) engaging with threaded holes 143 provided at the periphery of movable disk 134. The filter-type particle-capturing element 140 is preferably made of a pair of opposed rings 141, 141' for mounting therebetween with screws 135 a sheet of steel woven material 142 of a gage chosen according to the granulometry range of the collected particles. For a typical linting measurement application involving a paper web, a 20μ filtering material is preferably be used, as supplied by Madison Filter (Kirkland, Quebec Canada). The movable disk 134 is preferably provided with one or more further holders 144 each defining a central aperture extending through the disk 134, each being adapted to receive a flow calibration ring 146 secured by screws 148, the purpose of which ring will be explained later in detail. The movable disk 134 is also provided with a plurality of small perforations 179 that are regularly distributed near the outer periphery of movable disk 134 to provide reference optical channel for use with associated rotary position optical detectors the function of which will be explained later in detail. As shown in FIGS. 6a and 6b the first and second stationary plates 120, 122 are both provided with a pair of aligned small perforations 180' which are positioned in such a manner that corresponding small aperture 179 provided on the movable disk 134 can be simultaneously traversed by the beam of an optical position detector that will be described later with respect to FIG. 3.

Referring back to FIGS. 6a and 6b, the first and second stationary plates 120, 122 define a central axis 150 extending perpendicularly therethrough and along which sets of main apertures 130, 130' and 132, 132' are symmetrically disposed. Referring back to FIGS. 7a and 7b, it can be seen that the movable disk 134 is secured with a set of bolt assemblies 152 to a mounting portion 154 of a mechanical coupling element 156 receiving in rigid engagement therein a rotary shaft 157 having a reduced-diameter end portion 159 provided with an outer longitudinally extending rib 158 as shown in FIG. 8. Turning back to FIGS. 6a and 6b it can be seen that stationary plates 120, 122 are provided with central openings 161, 161' respectively aligned with central axis 150. The first stationary disk 120 is further provided at the periphery of a generally flat side 162 thereof with an innerly extending cut 164 whose dimension is sufficiently large to allow loading of a particle capturing element 140 on a corresponding holder 136 upon controlled displacement of the movable disk 134 so as to align receiving holder 136 with cut 164 shown in FIG. 6a. Conveniently, the second stationary plate 122 is also provided at the periphery of a generally flat side 162' thereof with an innerly extending cut giving clearance for the central portion of the capturing element holder 136 as shown in FIG. 7a when the movable disk 134 is located to its element loading position.

Turning now to FIG. 8, it can be seen that when the movable disk 134 is assembled in position between stationary plates 120 and 122, the opening 161 provided on stationary plate 120 is used to receive bolt 152 while the opening 161' provided on second stationary plate 122 is used to receive the mounting portion 154 of coupling element 156, thereby allowing the movable disk 134 to rotate within the gap 127 defined between first and second stationary plates 120, 122. In order to provided a sliding support for the movable disk 134, the handling assembly 118 further includes a bearing element 163 as well as a seat portion 165 adapted to receive a corresponding annular shoulder 167 provided on coupling element 156. The mounting portion 154 provided on coupling element 163 is rigidly mounted on the top portion 171 of support base 100 which entirely supports the weight of disk 134 so as to provide a substantially frictionless rotation thereof with respect stationary plates 120, 122. As better shown in FIG. 7b in view of FIG. 8, the assembly further includes a cylindrical coupling member 173 having an innerly extending bore defining a longitudinal recess 175 designed to receive the corresponding rib 158 of the reduced-diameter end portion 159 of rotary shaft 157. Turning again to FIG. 8, it can be seen that the speed reducer 116 is provided with an output rotary shaft 176 having an outer longitudinally extending rib 178 engaging with the recess 175 provided on coupling member 173 in such a matter that relative moment between rotary shafts 176 and 157 is prevented, so as to provide appropriate rotary mechanical coupling between the movable disk 134 and the rotary actuator 112 to allow thereof to impart a rotary movement to disk 134 about central axis 150.

Figure 4:
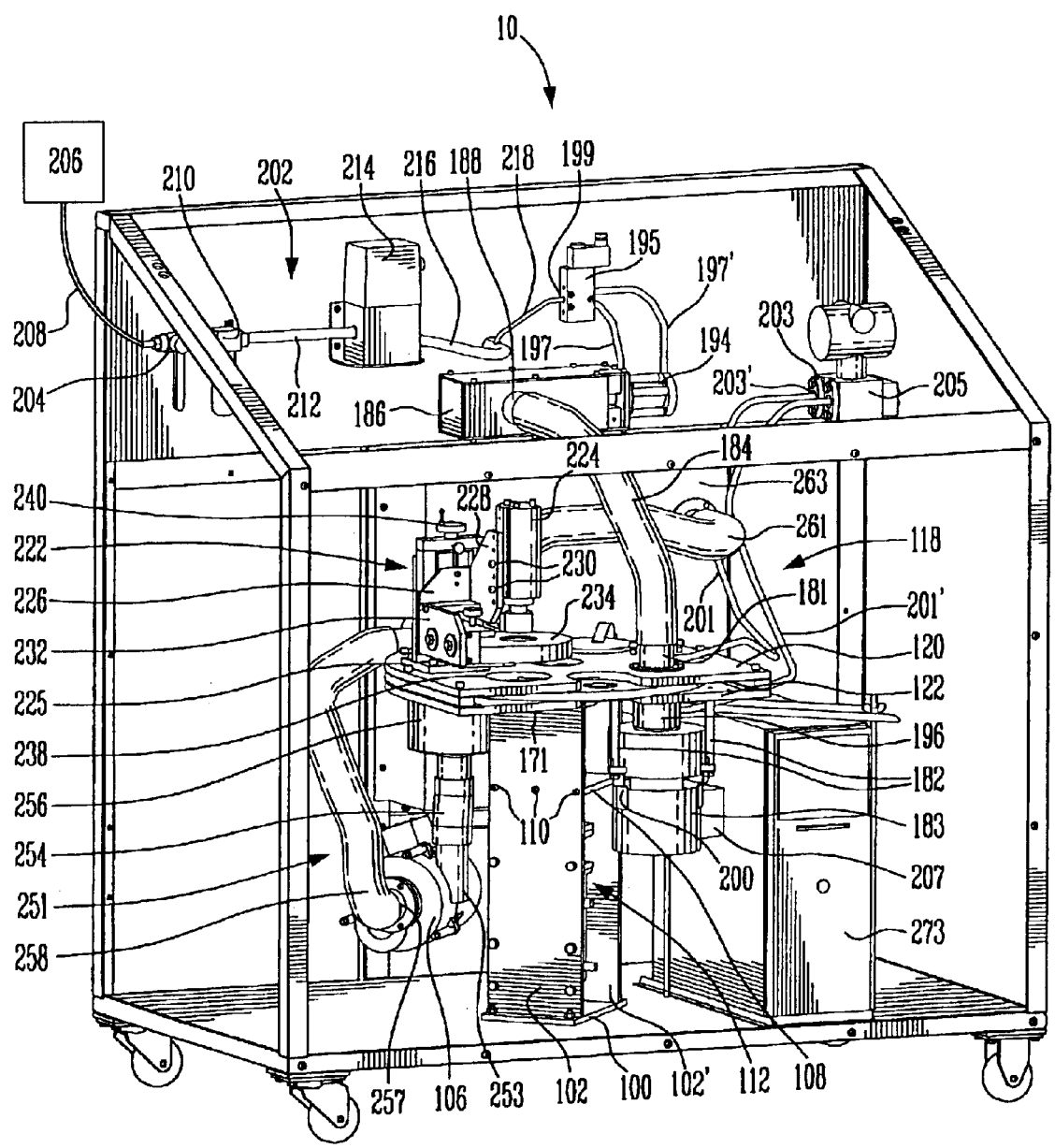
FIG. 4 is a further three-dimensional view of the apparatus FIG. 3 from a different angle illustrated with its front, top and opposed end panels being removed and without electrical/electronic enclosures to further show the various components of the apparatus.
Figure 5:
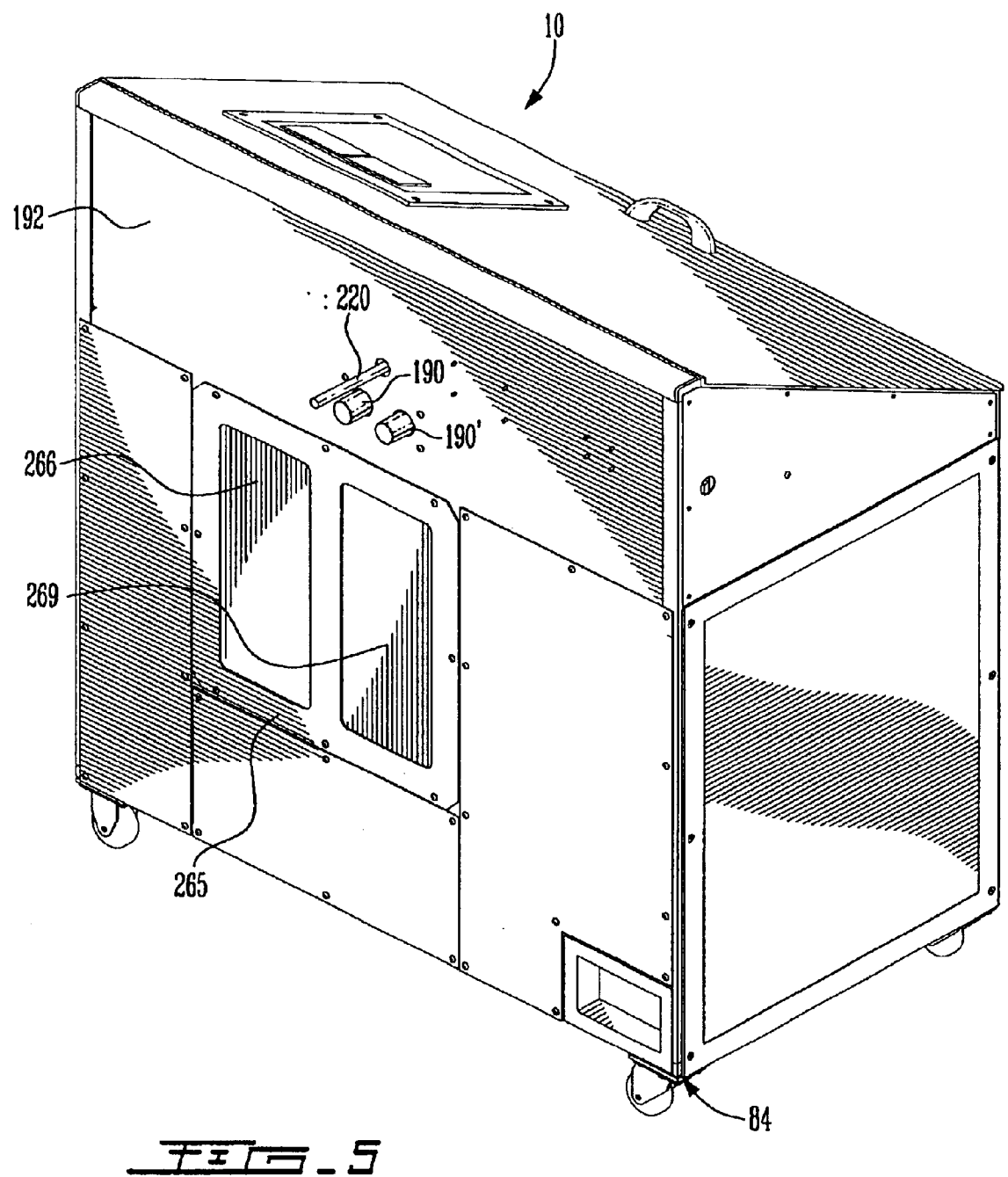
FIG. 5 is a still further three-dimensional view of the apparatus FIG. 3 showing filters and input-output conduits provided on the apparatus of FIG. 3.

Turning back to FIG. 6a in view of FIG. 3, the first main aperture 130 shown in FIG. 6a defines with a top flanged tubular coupling 181 a first inlet in fluid communication with an output fluid carrying line which is an air carrying line in the context of the present embodiment, which output air carrying line includes air conduit 184 that is coupled to the first and second conduit 16, 18 of the particle suction extractor shown in FIG. 1 using a pneumatically operated valve 186 provided with a single outlet formed by tubular coupling 188 and a pair of inlets formed by tubular couplings 180, 180' extending through a rear panel 192 affixed on the back portion of frame 84 as shown in FIG. 5. The valve 186 includes a movable deflector (not shown) mechanically coupled to a two-way controlled pneumatic cylinder 194 that is operable to displace the movable deflector between the first position where the inlet tubular coupling 188 is in air communication with outlet tubular coupling 190 which is itself connected through an external conduit (not shown) to output end 18 of first rigid conduit 16 transporting particles from collecting head 14 provided on suction extractor 12, and a second position wherein the same outlet tubular coupling 188 is brought in communication with inlet tubular coupling 190' which is itself connected to a further external conduit communicating with output end 18' of second conduit 16' transporting particles collected by second head 14'. The two-way function of pneumatic 194 is enabled by the use of a pneumatic valve 195 such as model no. MFH-5-1/8 from Festo having output air lines 197, 197' connected to pneumatic cylinder 194 to selectively apply pressurized air supplied to air input 199 from an air supply unit generally designated at 202 including an air entry valve 204 such as model no. QH-1/4 from Festo connected to an external pressurized air source such as air compressor 206 through air supply line 208. The valve 186 is capable of selectively coupling the first and second particle collecting heads 14, 14' to the air carrying line formed by air conduit 184 to allow conveying therethrough the particles collected from a selected one of first and second web surfaces 24, 84 shown in FIG. 1. An output of valve 204 is directly connected to an input port of a pneumatic filter 210 such as model no. LF-114-D-MINI from Festo which supplies filtered air through conduit 212 to a pressure regulator 214 such as model no. P3P-RJ92C106D from Parker for supplying through output conduit 216 pressurized air at a predetermined pressure level, typically of about 40 psi, to allow efficient working of the suction extractor as shown in FIG. 1 as well as adequate functioning of the control pneumatic cylinder 194 of valve 186 shown in FIG. 4. The output supply conduit 216 is provided with a junction connected to a first branch conduit 218 communicating with air input 199 of pneumatic valve 195 and having a main branch conduit 220 traversing the rear panel 192 attached to the apparatus frame 84 as shown in FIG. 5. The main branch conduit 220 is in turn connected to air supply conduits 35 and 35' respectively connected particle connecting heads 14, 14' as shown in FIG. 1.

Referring back to FIG. 3 and FIG. 4, the apparatus 10 further includes an optical sensing device generally designated at 222 preferably including an electronic camera 224 mounted on a support base 225 with a vertically displaceable mounting arrangement 226 having a first holding element 228 being adjustably secured to camera 224 using bolts 230 and a second holding element 232 adapted to adjustably secure an illumination device 234 using threaded rod handle 236. A high definition, 1235×1029 pixels, black & white electronic camera model TM-1300 from Pulnix may be used along with a 25 mm lens having a 6.5 mm collar, to allow X-Y resolution of 0.0025 cm/pixel on an imaged field of 3.2 cm×2.6 cm, with a lens-to-inspected surface distance of about 10 cm. The illumination device 234 is preferably a conventional annular lighting element such as a standard 25 kHz circular fluorescent tube defining central open area of a dimension larger than the optical vision field of camera 224 while directing light toward a secondary aperture 238 provided on first stationary disk 120 which is an optical alignment with camera 224. It can be seen from FIG. 4 that the support base 225 is provided with a rotary handle 240 mechanically linked to the mounting arrangement 226 to allow vertical position adjustment of both camera 224 and elimination device 234 so as to ensure optimal optical sensing conditions. As will be explained later in more detail, the optical sensing device 222 is capable of inspecting a selected particle capturing element to generate a measurement signal representative of optical characteristic of the collected particles as captured by that selected element.

Turning back to FIG. 6b, it can be seen that the secondary aperture 238 is located on first stationary disk 120 at a distinct angular position with respect to first and second main apertures 130, 130', to allow selective displacement of the movable disk 134 between a particle capturing position and an capturing element inspecting position as will be explained later in more detail. Although the second stationary element 122 is preferably provided with a corresponding aperture 242 that is aligned with secondary aperture 238, it can be seen from FIG. 6b that a covering plate 244 is disposed underneath stationary plate 122 to entirely cover aperture 242 in the embodiment shown, the aperture 242 being necessary when an optical sensing device using underneath elimination particle capturing elements is employed according to an alternate embodiment of the invention. As it can also be seen from FIG. 6a there is provided on first stationary disk 120 a further aperture 246 that is similarly aligned with a corresponding further aperture 248 provided on second stationary disk 122 which is also covered by a further covering plate 248 as shown in FIG. 6b. Further aperture 246 and 248 are optionally provided so as to allow the incorporation of an additional operating station on the handling assembly 118, such as microscopic inspection station (not shown) that could be used for performing complementary analysis of loaded particle capturing elements. As shown in FIG. 4, whenever such additional station is not used, a further covering plate 250 is disposed on top of first stationary disk 120 in alignment with further aperture 246, as better shown in FIG. 3.

Turning back to FIG. 6b in view of FIG. 4, the second main aperture 132 provided on second stationary plate 122 defines with an underneath flanged tubular coupling 196 which is itself connected to the air suction intake of vacuum air blower 183, such as model no. 117728-00 form Ametek, a first inlet to provide fluid communication with the output fluid carrying line through the corresponding channel defined by line main apertures 130, 132 and extending through the gap 127 as shown in FIGS. 6a and 6b. Top and underneath flange tubular couplings 181, 196 are respectively connected to conduits 201, 201' to provide air communication with respective inlets 203, 203' provided on a differential pressure probe 205 such as model no PX771 from Omega. As will be explained later in more detail, the differential pressure probe 205 is periodically used to calibrate the air suction flow produced by electrical vacuum air blower 183 to a predetermined value to insure that each particle capturing element is being subjected to a same suction pressure providing stable and efficient particle collecting. For so doing, the electrical vacuum air blower 183 is provided with a speed variator contained in the electrical enclosure 207 to allow adjustment of input electrical power fed to the vacuum air blower 183 in accordance with the set calibration differential pressure value. The apparatus further includes a capturing element cleaning device as generally designated at 251 provided with a cleaning fluid source which preferably uses air as cleaning fluid by means of vacuum air blower 106 as shown in FIG. 4 having an air outlet 253 being coupled through tube section 254 to a second underneath flange tubular coupling forming which defines with second aperture 132' as shown in FIG. 6b a second inlet providing a fluid communication with a cleaning fluid carrying line formed by tube section 254, blower air outlet 253 and air intake conduit 258 connected to air suction inlet 257 of vacuum air blower 106. As better shown in FIG. 3, the cleaning device 251 further includes a second top flange tubular coupling 260 affixed to the surface of the first stationary disk 120 to define with a corresponding second main aperture 130' as shown in FIG. 6a a second outlet for providing fluid communication with the cleaning fluid carrying line through a corresponding channel extending through the gap 127 separating first and second stationary disk 120, 122. Connected to the second top coupling 260 is an air collecting conduit 261 as part of the cleaning fluid carrying line to convey air with particle removed from the particle capturing element subjected to cleaning toward a particle receiving compartment of an enclosure 263 having a back wall 265 provided with an exhaust filter 266 made of an appropriate fabric allowing forced air to be released therethrough while preventing collected particles from exiting the receiving compartment of the enclosure.

Turning back to FIG. 4, it can be seen that the air intake conduit 258 is provided with an inlet end 267 connected to a second compartment of enclosure 263 which communicates with air intake filter 269 affixed to the back wall 256 as shown in FIG. 5. It is to be understood that according to a variant of the cleaning device provided on the embodiment shown, the vacuum air blower 106 can be arranged in a position downstream from the second outlet defined by second main opening 130' provided on first stationary disk 120 as shown in FIG. 6a and the second top tubular coupling 260 as shown in FIG. 3 according to an air suction configuration for a same claiming purpose, wherein the air intake conduit 258 is directly coupled to the second inlet 256 underneath second stationary plate 122 while the air collecting conduit 261 receives the coupling tube section 254 to complete the cleaning fluid carrying line.

Turning again to FIG. 3, affixed to the top surface of first stationary plate 120 is a light beam emitting component 271 as part of an optical position detector and aligned with small aperture 180 provided on first stationary plate 120, which detector further has a complementary photocell based receiving component (not shown) affixed underneath the second stationary plate 122 in alignment with small aperture 180' as shown in FIG. 6b. The apparatus 10 further includes a data processor in the form of a personal computer (PC) 253, the function of which will be described below with reference to FIGS. 9 and 10. The PC 253 used in the present embodiment includes a Pentium III™, 256 Meg RAM, CR-RW with 40 gig. hard disk, using a digital frame grabber model Meteor II™ from Matrox (Dorval, Quebec, Canada).

Referring now to FIG. 9, the control and data processing sub-system as part of the preferred embodiment can be generally described as including PC 273 connected through a bus line 275 to the optical sensing device 222 and also connected through a bus line 278 to a data input-output unit 277. Data exchange with control terminal 96 is provided through bus line 280, and status data is sent to a staus pilot through activating line 282. Differential pressure indicative signal as generated by pressure probe 205 is fed to input/output unit through line 281, while exchange of control and pressure measurement data with pressure regulator 212 is provided through line 283. As shown in FIG. 3, the control terminal 96 is conveniently provided with two displays 97 for indicating measured differential pressure and supplied pressure value fed to the suction extractor as set by pressure regulator 212. The control terminal 96 is preferably provided with a selector device, allowing an operator to select the desired operating mode such as start, stop and calibration modes. Furthermore, a status pilot 281 a shown in FIG. 9 giving an indication of the operation status of the apparatus can be separately provided or integrated into the control terminal 96. The control terminal 96 can also be provided with an emergency stop command and with a further command providing initialization of a programmed measurement cycle to be performed by the apparatus. The apparatus further includes as part of the sub-system shown in FIG. 9, a controller in the form of a programmable logic controller (PLC) such as model 1000 32 I/O from Micrologix which PLC 283 is operatively connected to the actuator 112 as described above with respect to FIGS. 3 and 4 using a suitable actuator drive 284 through forward and reverse motion control line 286, 286', which actuator drive 284 sending synchronization signal back to PLC 283 using line 288. The PLC 283 has also the function of controlling the operation of the pneumatic valve 195 which in turn controls operation of the pneumatically operated valve 186 providing selection of a particle collecting head as explained before with respect to FIGS. 1 and 4, using a control line 290. Synchronization signals coming from actuator drive 284 are transferred by PLC 283 to the personal computer 273 through line 291, data input/output unit 277 and bus line 278. In turn, the data input/output unit 277 is programmed to generate a PC status indicative signal to the PLC 283 through data line 293. Conveniently, the data input/output unit 277 may communicate through line 295 a system status indicative signal toward a further PLC 296 controlling a paper machine in operation within the manufacturing plant, to either prevent or interrupt machine operation whenever an off-system status signal is received by plant PLC 296. Reciprocally, an off-operation indicative signal received by the data input/output unit 277 from PLC 296 through line 297 may cause the PC 273 to send through input/output unit 277 and line 293 an interruption signal toward PLC 283 which stop the actuator through drive 284 accordingly. The data input/output unit 277 may be selected from commonly available data acquisition products available in the marketplace such as the FieldPoint™ supplied by National Instrument provided with appropriate communication and input/output modules as can be readily selected by anyone skilled in the art. The two complementary binary signals generated by the PLC 283 and sent to the data input/output unit 277 allow up to four acquisition states, namely interrupted state, particle-free measurement state, pressure calibration state and particle-loaded element measurement state. So as to complete the acquisition state requested by the PLC 283, the latter further generates through control line 292 a paper web surface indicative signal in accordance with the selected particle-capturing head in operation, as set by the PLC 283 through line 290 connected to pneumatically-operated valve 186. To enable the requested acquisition state, the PLC 283 further sends to PC 273 through data input/output unit 277 the drive status indicative signal as received from the actuator drive 284 through line 288.

Figure 10:
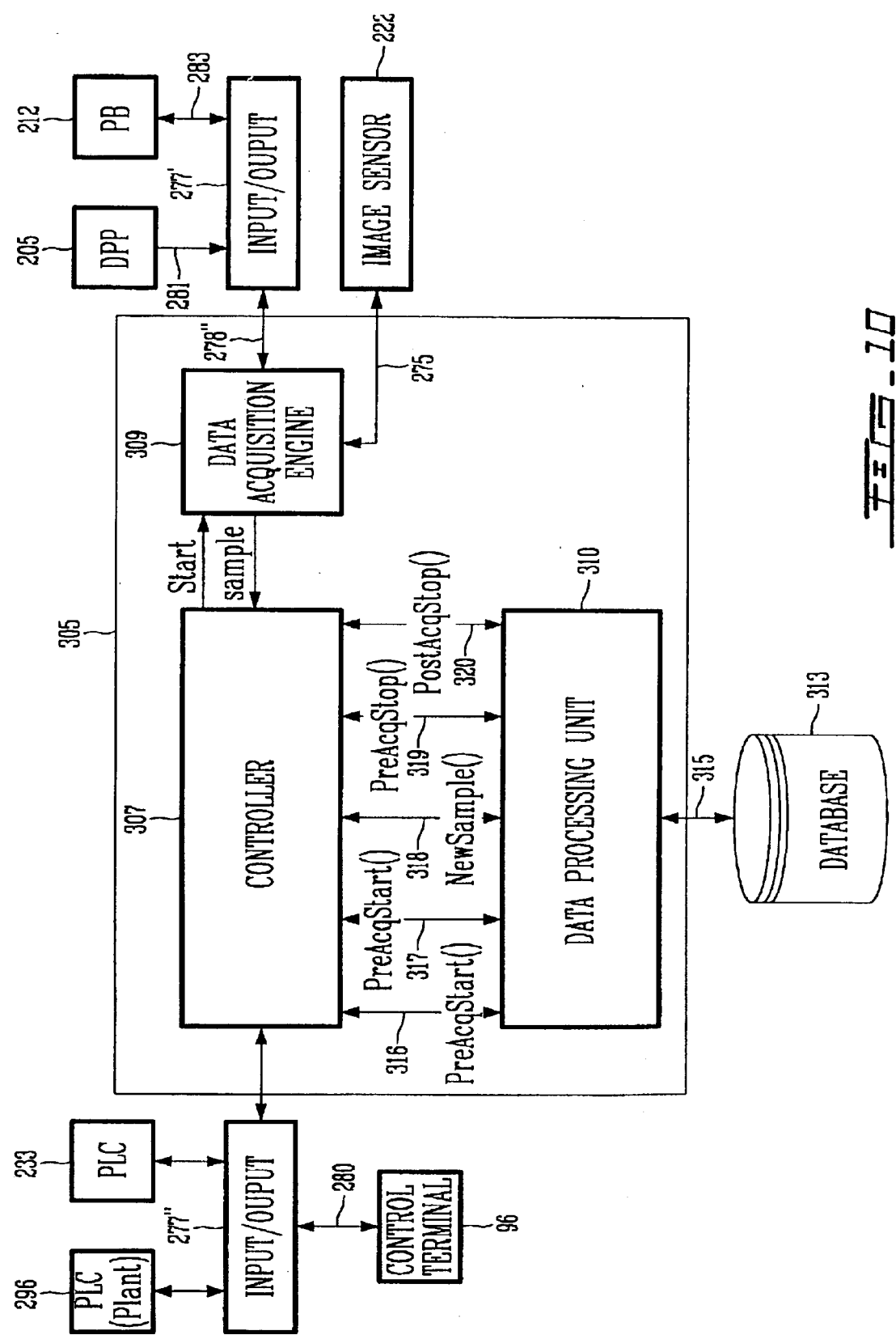
FIG. 10 is a detailed block diagram of the controlling and data processing module implemented in the personal computer shown in FIG. 9.

Referring now to FIG. 10, the control and data processing module implemented in the PC 273 will now be described in more detail. Referring now to FIG. 10, a more detailed description of structure and operation of the control and data processing module will now be presented. It is to be understood that any other suitable architecture may employed, the control and data processing functions of the apparatus according to the preferred embodiment of the invention is conveniently software-implemented in the PC 273. The idea behind such architecture is to develop a generic data acquisition engine to which are connected the various sensors, control and analysis components, and in which the acquisition code is separated from the analysis code, the latter being specific to the application. Preferably, to provide a maximum flexibility of use, DCOM architecture from Microsoft Corp. has been used, which architecture provides, among other features, geographic distribution of the components, which are Visual Basic and Visual C++ based components. The control and data processing module as generally designated at 305 in FIG. 10 is structured in several components that are interconnected to provide data acquisition management from differential pressure probe 205, pressure regulator 212 through a first input/output module 277' and line 278' provided on the data input/output unit 277 shown in FIG. 9. The module 305 basically comprises a controller 307, a data acquisition engine 309 and a data processing unit 310. The controller 307 is linked to the PLC's 233 and 296 as well as control terminal 96 through a second input ouput module 277" and line 278" provided on the unit 277 shown in FIG. 9. Conveniently, measurement signals from the image sensor 22 and control signal sent thereto can be directly exchanged through data acquisition engine 309 using bus line 275. Finally, a database 232 for storing resulting estimation data may be advantageously provided and linked to the data processing unit through data line 315.

The purpose of controller 307 is to manage the activity of the whole control and data processing module. Preferably, the controller 307 is in the form of a COM object implemented in the PC as an executable server. The controller 307 receives commands from PLC's 233, 296 which connect to controller 307 so as to feed thereto commands and to receive therefrom data as required from probes 205, 212. During the acquisition process, new samples are simultaneously sent to PLC's 233, 296 connected to controller 307. In that way, each one of PLC's can then process a received sample as desired. At each acquisition cycle, the controller 307 interrogates each probe 205, 212 and image sensor 22 that are connected thereto. The controller 307 is also used to transfer sample consisting of sensed data to the data processing unit 310. It is to be understood that the controller 307 does not perform data processing or analysis on the basis of data received from probes 205, 212 or image sensor 222. Data analysis is rather done by the data processing unit 310 as will be described later in detail. Once the data processing unit 310 has finished the analysis of a sample, the latter is returned to controller 307 which in turn has the task of sending the sample to PLC's connected to controller 307. To perform its task, the controller 307 makes interaction with its hardware and software environment for providing services thereto. Communication with the controller 307 is provided by specific interfaces that gather services provided by the controller 307. Conveniently, there is provided a configuration interface, an operating interface and an internal use interface. The configuration interface allows adding or withdrawal of sensors such as probes 205, 212 and image sensor 222 used in an acquisition process and acquisition frequency update. The operation interface gathers the tasks that are used by the PLC's to feed commands to the controller 307. Among these tasks are included controller subscription or acquisition start/stop services. The internal use interface is solely solicited to provide communication between controller 307 and the data processing unit 310. For example, the internal use interface allows the data processing unit 310 to ask controller 307 to send an alarm message to PLC's whenever abnormal system status is detected. The data processing unit 310 performs sampled data analysis following an acquisition, to generate an estimation of the quantity of particles captured by an inspected capturing element, as will be explained later in detail. The data processing unit 310 also manages interaction with database 313 whenever estimation data have to be stored. The communication between the data processing unit 310 and controller 307 is provided through an information exchange protocol conveniently using five different communication subroutines described below with reference to FIG. 10. "PreActStart": this subroutine represented at 316 is called by the controller 307 whenever the latter receives an acquisition start command from PLC's. This subroutine is used to initialize the system before starting a new acquisition.

"PostAcqStart": this subroutine represented at 317 is called by the controller 307 immediately after the starting of a new acquisition. Upon calling of the subroutine, the controller 307 provides to the data processing unit 310 a unique number corresponding to the data acquisition that is starting. For example, the data processing unit 310 can read administrative data stored in a file by PLC 296 and then make a link in the database 315 with the unique identification number corresponding to the current acquisition.

"New sample": this subroutine represented at 318 is called by the controller 307 whenever a new sample is ready. It is used to process the new sample so as to compute statistics such as histograms or to store sample data in database 313. In response to the subroutine call, the sample is automatically sent by the controller 307 to PLC's connected thereto.

PreAcqStop: this subroutine represented at 319 is called by the controller 307 whenever it receives a stop acquisition command from either PLC's.

PostAcqStop: this subroutine represented at 320 is called by the controller 307 immediately after an acquisition is finished. This subroutine can be used to close an acquisition process, for example by computing statistics about the acquisition process which has finished.

A main feature of the present architecture consists in using a generic sample as a means for exchanging sample data within the module 305. This generic sample allows module components to be independent from one another. Conveniently, as for other main components of the module, the generic sample is based on the DCOM architecture from Microsoft Corp. The generic sample consists of a plurality of types of data, including measurement data. Such data is either read by probe 212 or image sensor 222, or otherwise computed by the data processing unit 310. An example of data structures is as follows:

ID sensor: identification code of the probe or sensor that has generated measurement data;

ID measure: identification code for the data as read by the probe or sensor;

Measurement value: code representing measurement value;

Measurement description: brief description of the measurement;

Measurement unit: identification code of the measurement unit (psi)

Simulation: parameter indicating if a simulated/actual measurement is involved;

Validity: parameter indicating if measurement data is valid or not;

Alarm tag: directed to alarm object including detailed information about a generated alarm.

The generic sample includes a single interface within which are gathered all services provided, such as for adding or withdraw data from a specific sample. A measurement searching service is also provided in the sample by which a search is performed by asking to the sample specific measurement data corresponding to a unique identification number used as a search parameter. The data acquisition engine 309 is used by probes 205, 212 and image sensor 222 to enable feeding of the controller 307 with data according to a specific communication format as requested by the controller 307. Therefore a data request protocol between the controller 307 and probes 205, 212 or image sensor 222 allowing communication between the different components of the module 305 must be implemented. Such communication protocol is provided by sensor management sub-modules that are implemented in the acquisition engine 309. The sensor management sub-modules are developed in the form of executable servers which are based on a DCOM architecture providing maximum flexibility. The sensor management sub-modules are passive components which are responsive to commands from controller 307 or any of PLC's 296, 233 and control terminal 96. Conveniently, each sensor management module includes a configuration interface, a calibration interface and an operation interface. The configuration interface gathers a set of services providing updating and interrogation of probe/sensor configuration values, which services are different for each sensor. For example, the management unit for image sensor 222 may provide services for updating file folders for calibraton. The calibration interface is required for all sensors that need software-based calibration. The operation interface is governed by very strict rules since it is used by the generic acquisition management of the controller 307. Hence, each probe or sensor must be responsive to controller commands in the same way. Furthermore, adding a new type of sensor such as an additional microscopic camera for providing specific particle or fibre analysis, would not require any modification to the acquisition management function of the controller 307. Typically, the operation interface provides the following services:

"Init": This service allows to make an initialization request from the sensor management unit. Upon calling of this service, the probe/sensor is initialized using configuration parameters that were previously selected by means of the configuration interface discussed above.

"Get data": This service allows to make a request to a specific probe/sensor for generating measurement data. This service is called by the controller 307 so that all sensors must respond in the same way so as to preserve generic characteristic of the system. So as to comply with the different interdependence requirements of the different sensors, the generic sample is parameterized. Any sensor may then interrogate the sample so as to extract data as needed. Once the sensor management modules have performed a desired measurement, they add the acquired data to the generic sample. Such principle of operation provides a communication which respects generic characteristic requirements while offering the capability of respond to all interdependence requirements of the sensors. A preferred mode of operation of the embodiment of the present invention as hereinabove described will now be explained in detail with reference to FIGS. 11a–11l in view of FIGS. 1–9, further in view of FIGS. 12a–14b. In FIGS. 11a–11l the movable disk 134 is shown in various positions according to a complete cycle of operation involving up to four particle-capturing elements has designated by numeral 1-4 in FIGS. 11a–11l with respect to four operating positions evenly distributed about the central axis 150 in 90° index increment, namely: (1) element inspecting, (2) element cleaning, (3) optional and (4) particle-capturing position, respectively corresponding to: (1) optical sensing device 222, (2) capturing element cleaning device 251, (3) optional station covering plate 250 and (4) opposed tubular couplings 181, 196 affixed to stationary plates 120, 122.

Figure 11A:
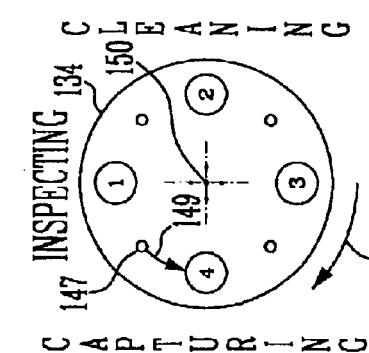
FIGS. 11a–11l are schematic representations of the handling assembly provided on the apparatus of FIG. 3 in successive operation sequences in the handling of a plurality of particle capturing elements.

Prior to start measurement cycles, the operator commands activation of first and second cylinders 72, 72' provided on the adjustable holder 50 shown in FIG. 1 to bring the collecting heads 14, 14' to an appropriate working position onto and beneath surfaces 24 and 84 of the paper web 19 in a manner as shown in FIG. 2. Then, the operator enters via control terminal 96 a command addressed to PLC 283 for performing calibration of the particle-capturing pressure created by the vacuum air blower 183 which is in communication with the air carrying line via couplings 196, 181 and air conduit 184 through a corresponding channel traversing gap 127. For so doing, the PLC 283 sends through line 286 a command to the actuator drive 284 to perform rotation of the movable disk 134 until the light beam emitted by component 271 of the optical position sensor is received by its corresponding receiving component whereby an appropriate position reference is set. Thereafter, the calibration operation continues with a further command to the actuator drive 284 to rotate the movable disk 134 to a positive 45c so as to bring one of flow calibration rings 146, whose central hole 147 is represented on FIGS. 11a–11l, in alignment with the capturing position as indicated by counter-clockwise arrow 149 on FIG. 11a, allowing the operator to adjust the speed variator provided on vacuum air blower 183 to a preset differential pressure value as measured by the differential pressure probe 205 indicated by corresponding one of displays 97 provided on control terminal 96. It has been experimentally found that a measured differential pressure value of about 25 to 30 psi corresponds to a flow that is adequate to provide efficient particle collecting. After the calibration operation is completed, the operator commands the execution of a continuous programmed operation cycle by the PLC 283, according to which alternate measurements of both web surfaces 24 and 84 are performed, wherein PLC 283 activates pneumatic valve 199 and sends a web surface indicative signal to PC 273. The PLC 283 generates a forward control signal via line 286 to the actuator drive 284 so that a first particle-free capturing element represented at "1" in FIG. 11a is brought to the inspecting position in the clockwise direction of arrow 297. Then, the PLC 283 generates corresponding synchronization binary signals through lines 291, 291' indicating to the PC 273 that a particle-free element is to be measured, causing the PC 273 to receive from optical sensing device 222 through bus line 275 a reference signal representative of optical characteristics of the first particle-capturing element substantially free of particles. Then, the PC 273 receives for analysis the reference signal to generate a calibrating signal corresponding to a substantially zero quantity of particles on the first inspected element "1". It as been experimentally found that an inspecting period of time of about five (5) seconds is appropriate using the Pulnix TM-1300 camera used in the preferred embodiment as hereinabove described.

Figure 11B:
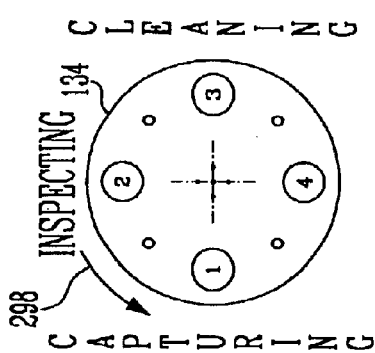

Turning now to FIG. 11b, the PLC 283 sends a reverse control signal through line 286' to the actuator drive 284 so as to rotate the movable disk 134 in the counterclockwise direction of arrow 298 so that the capturing element "1" is interposed within the output fluid carrying line, wherein one of the holders 136–139 supporting the capturing element "1" is aligned with the first inlet and outlet formed by main apertures 130, 132 as shown in FIGS. 6a and 6b so that correspondingly received particle capturing element "1" captures the particles during a first predetermined period of time. It has been experimentally found that a capturing period of time of about forty (40) seconds is sufficient to load a particle capturing element such as the 20μ element as described before, to obtain image data that can be processed in a reliable manner.

Figure 11C:
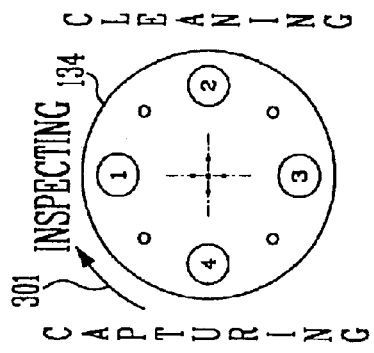

In a following step shown in FIG. 11c, the PLC 283 displaces the movable element in the clockwise direction of arrow 301 from the first capturing position to a second position where said the holder having the selected capturing element "1" received therein is aligned with the secondary aperture 238 shown in FIG. 6a so as to be inspected upon operation of the optical sensing device 22 during a second period of time, typically five (5) seconds. Then, the PC 273 proceeds with analyzing the measurement signal to generate an estimation of a quantity of particles captured by the element "1". This analyzing step is performed by comparing the measurement signal with the reference signal to generate the desired estimation in a manner that will be now explained in detail with reference to FIGS. 12a–14b.

Preferably, the reference signal and measurement signal generated by the optical sensing device 222 are representative of optical characteristics of a free-particle capturing element and the same capturing element after being loaded with particle, respectively, the optical characteristics being preferably expressed in term of reflectance measurement of a clean or substantially free-particle capturing element on the one hand and of the particles captured on the surface of the same particle-capturing element following positioning thereof within the output fluid carrying line during the first predetermined period of time on the other hand. Preferably, the analyzing step consists of evaluating only the image density that can be attributed to the particles while discarding portion of the image data that can be attributed to the surface of the capturing element itself. Therefore, image data must be segmented to differentiate particle associated pixels and surface-associated pixels. So as to obtain a reliable particle density measurement, such measurement must be preferably independent of luminance variability among those particles. Furthermore, the particles and capturing surface must exhibit luminance characteristics sufficiently different so as to allow segmentation with one another. It is also pointed out that to compensate for any illumination variation, a suitable image calibration is performed in a manner well known by anyone skilled in the art. The comparison between the measurement signal and the reference signal is preferably performed using pixel intensity histograms as shown in FIGS. 12a and 12b. The reference histogram represented at FIG. 12a allows signature identification of the particle-free capturing element. Comparing with the histogram constructed from measurement signals obtained with the same capturing element loaded with particles, it can be seen that the first histogram portion 299 below a threshold intensity value of 121 substantially corresponds with the whole area 299' of the histogram represented at FIG. 12a. Assuming that there is a sufficient luminance gap between capturing surface of each element 140 and the particles, the pixels associated with an intensity value beyond the threshold value of 121 as part of the portion 300 of the histogram illustrated at FIG. 12b can be considered as corresponding to the particle measurement portion of the image data, so that corresponding number of pixels may be cumulated by the data processor of the PC 273 to provide a variable estimation of the quantity of particles captured by the inspected element. Conveniently, the threshold value can be derived from the histogram of FIG. 12a by determining the intensity value for which a predetermined minimal percentage of pixels have a value higher than that threshold value.

Figure 13A:
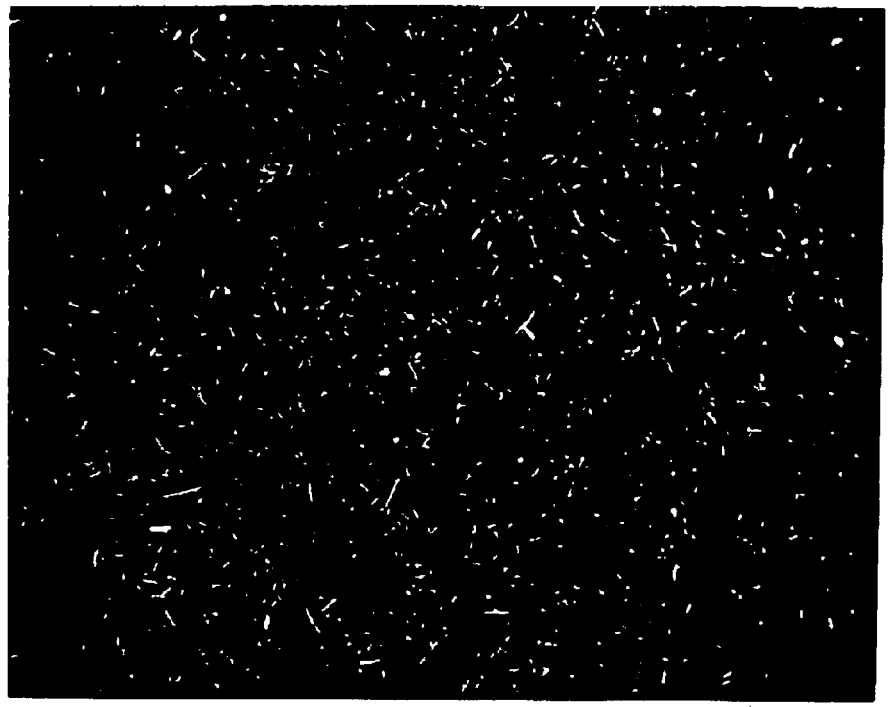
FIG. 13a represents a raw image as obtained by the optical sensing device provided on the apparatus of FIG. 3 using a dark-colored filtering medium.
Figure 13B:
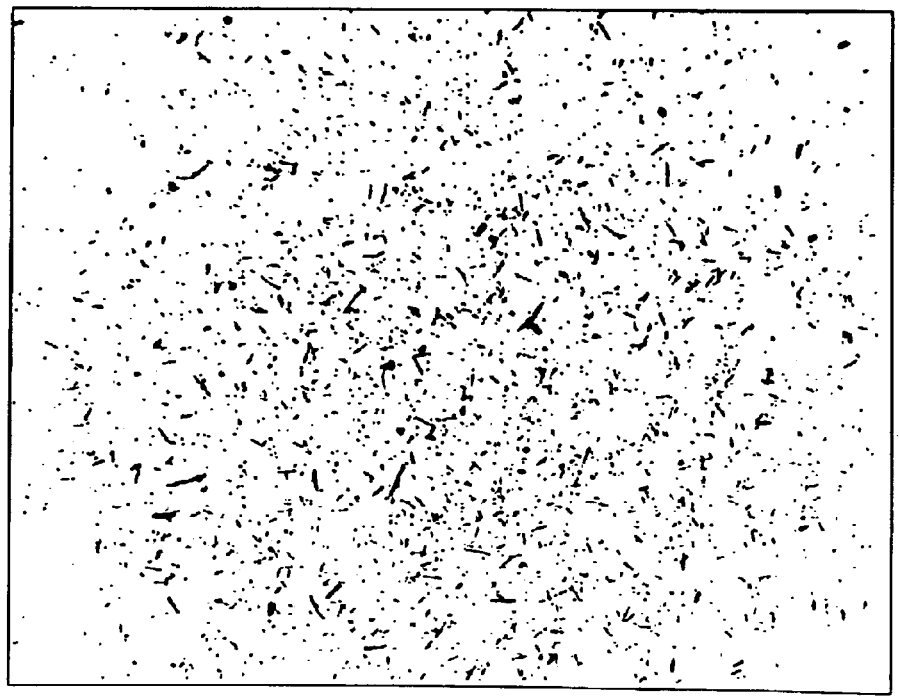
FIG. 13b represents a processed version of the image shown in FIG. 13a in which pixels of the image attributed to sensed particles have been subjected to a binarization processing step to allow particle quantifying as performed by the method of the invention.

Referring now to FIG. 13a, a raw image obtained with a dark capturing element is illustrated, showing light particles as captured by the dark-colored surface of the capturing element. Turning to FIG. 13b, a binarized image obtained after comparison with the reference image data is shown in opposed contrast, allowing pixels counting to estimate the particle image density as an indication of the quantity of particles captured by the element.

Figure 14A:
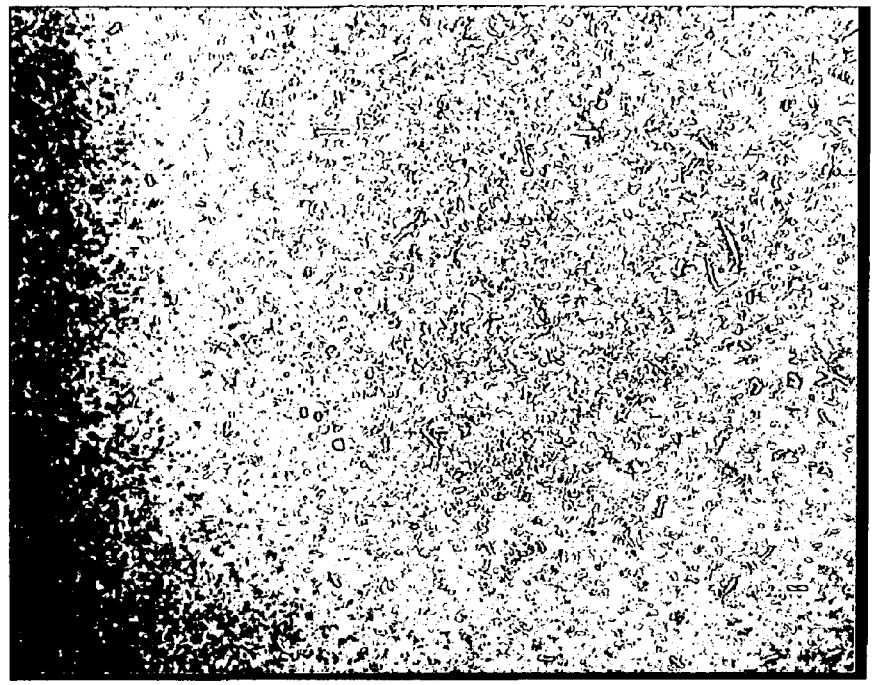
FIG. 14a represents a raw image as obtained by the optical sensing device of the apparatus of FIG. 3 using a light-grey colored particle capturing element.
Figure 14B:
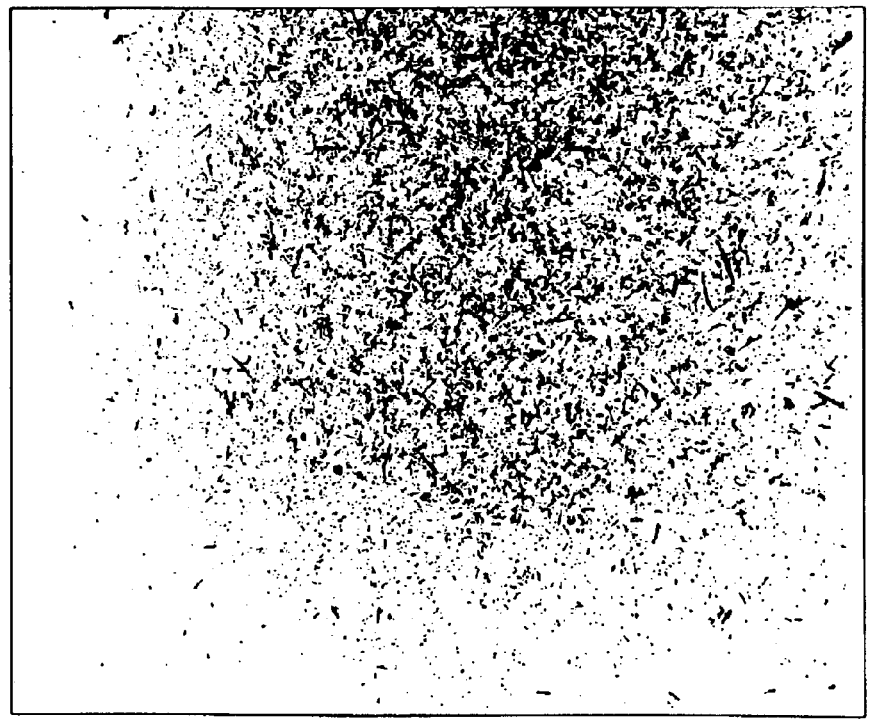
FIG. 14b presents a processed version of the raw image of FIG. 14a as obtained by applying a binarization processing step according to the method of the invention.

Turning now to FIG. 14a, a raw image as obtained with a light-grey colored particle-capturing element loaded with a given quantity of particles is shown. Although the reduced luminance contrast obtained with this alternate filter as compared with the high contrast obtained with the dark element referred to above, it can be seen from the binarized processed image shown in FIG. 14b that a reliable estimation of the quantity of particles accumulated on the surface of the capturing element can be derived using the same histogram-based technique described above. It has been experimentally found that there is a clear correlation between the measured particle image density as observed for a particle-capturing element loaded with particle after a predetermined period of time and the actual quantity of particles that can be measured by a reference conventional weighing technique.

Turning again to FIG. 11b, it can be seen that while the first particle-capturing element "1" is interposed within the output fluid carrying line in a capturing position, the further particle-capturing element 3 "is" aligned with the cleaning device whereby cleaning fluid removes the captured particles upon circulation through the cleaning channel simultaneously to the capturing operation performed on the capturing element "1". In other words, at least two of holders 136–139 are located on the movable element 134 so as to be simultaneously aligned with first inlet and second inlet respectively upon controlled movement of the movable element 134. In a continuous mode of operation, when the element "1" is the capturing position, an other holder has a previously inspected element "3" correspondingly received therein and aligned with the second inlet and outlet so as to be cleaned upon operation of the cleaning device.

Figure 11D:
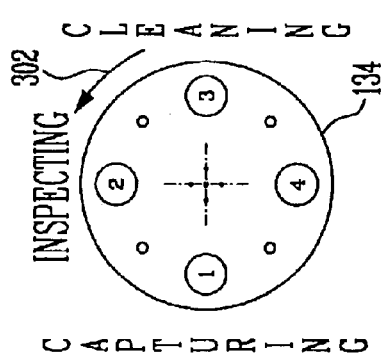
Figure 11E:
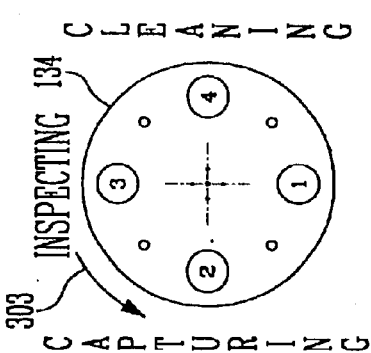
Figure 11F:
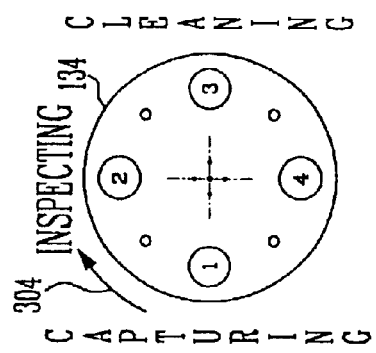
Figure 11G:
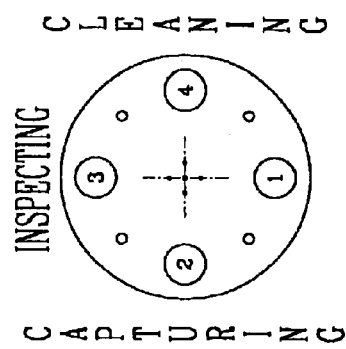
Figure 11J:
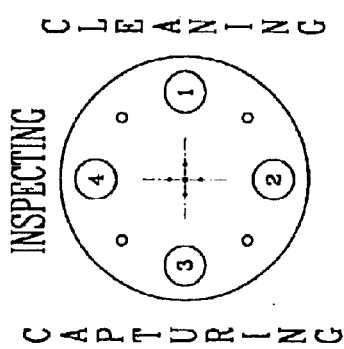
Figure 11H:
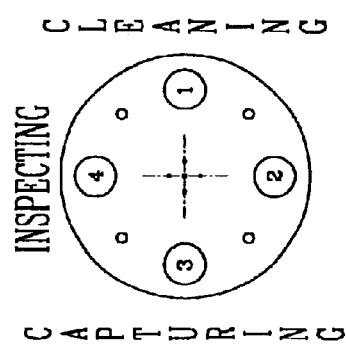
Figure 11K:
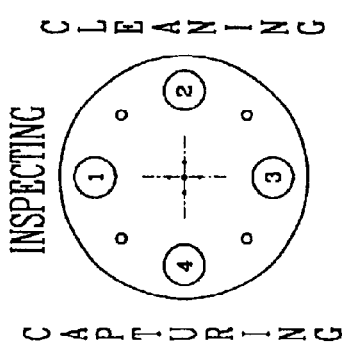
Figure 11I:
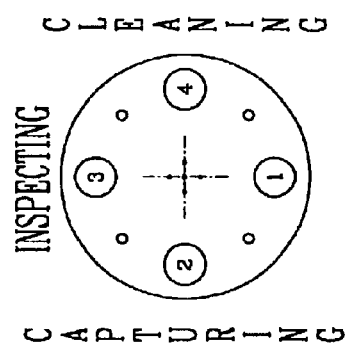
Figure 11L:
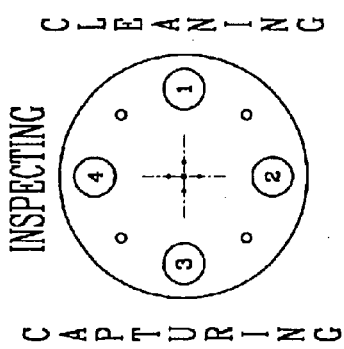

Turning now to FIG. 11d, a second sequence of the operating cycle consists of displacing the particle-capturing element "2" in an inspecting position in the counterclockwise direction of arrow 302 according to a 90° index increment for performing an inspection of element "2" having a substantially zero quantity of particles thereonto. Turning now to FIG. 11e, in a similar manner as explained above with reference to FIG. 11b, the movable disk 134 is then displaced under the control of PLC 283 and actuator drive 284 in a counterclockwise direction indicated by arrow 303 so as to bring the capturing element "2" in communication with the output fluid carrying line for particle capturing during the predetermined period of time as set forth before. As shown in FIG. 11f, the second sequence of the operating cycle is completed by bringing the capturing element "2" back to the inspecting position in the clockwise direction indicated by arrow 304 in a same manner as explained before with respect to FIG. 11c. According to a third sequence of the operating cycle, illustrated in FIGS. 11g–11i, the third capturing element "3" is successively brought from a first reference inspecting position, to a capturing position and back to an inspecting position after being loaded with particles. A final sequence of the operating cycle is shown in FIGS. 11g–11l regarding a fourth particle-capturing element "4". Then, the operating cycle is repeated so as to obtain a substantially continuous estimation of the quantity of particles collected from surface of the paper web under measurement. It can be seen from FIG. 11, that the first particle-capturing element "1" is brought to a cleaning position at the end of the fourth sequence just before being again inspected at the beginning of the first sequence shown in FIG. 11a wherein a particle-free element reading is performed.

It is to be understood that the scope of the present invention is not limited to the preferred embodiments of apparatus and method for quantifying particles as described hereinabove, and that either variants of these embodiments or alternate embodiments may be considered as encompassed by the invention as defined in the appended claims. For example, according to a variant of the optical sensing device, the latter may be adapted to the measurement of optical transmission characteristics of the inspected capturing element, by providing the handling assembly with an underneath illumination device for directing light through the capturing element, to allow transmitted light to reach the electronic camera, and the image analysis performed by the data processor can be adapted accordingly. According to an alternate embodiment, the movable element of the capturing element handling device may be formed of an elongated sliding plate wherein the apertures are provided according to a linear configuration. The first and second stationary elements may be provided with a corresponding linear configuration of apertures. Providing a linear actuator rather than a rotary actuator, a reciprocal displacement between capturing, inspecting and cleaning positions may be obtained. Alternatively, the movable element of the capturing element handling device may be formed of an annular structure on which the apertures radially extend according to a circular configuration about a central axis. The first and second stationary elements may be in the form of concentric annular structures each provided with a corresponding circular arrangement of radially extending apertures, forming an annular gap therebetween for receiving the movable annular structure. A rotary actuator coupled to the movable structure would provide rotation thereof about the central axis to allow controlled movement between capturing, inspecting and cleaning positions.

We claim:

1. An apparatus for estimating the quantity of particles collected by a suction extractor through an output fluid carrying line provided thereon, comprising:

a capturing element handling assembly including first and second stationary elements disposed in a spaced relationship to define a gap therebetween, said stationary elements being provided with respective sets of main apertures disposed in alignment with each other to define a corresponding set of channels extending through the gap, a movable element interposed within the gap and being provided with a plurality of holders capable of receiving a plurality of filter-type particle capturing elements, and an actuator operatively coupled to the movable element for providing controlled movement of the movable element relative to the stationary elements, wherein one said main aperture on the first stationary element defines a first inlet in fluid communication with the output fluid carrying line and one corresponding said aligned main aperture on the second stationary element defines a first outlet for fluid communication with the output fluid carrying line through a corresponding said channel;

an optical sensing device disposed in alignment with a secondary aperture provided on the first stationary element and extending therethrough to communicate with the gap, for inspecting a selected one of said particle capturing element to generate a measurement signal representative of optical characteristics of the collected particles as captured by the selected element;

a data processor for analyzing said measurement signal to generate an estimation of the quantity of particles captured by the selected element; and a controller operatively connected to the actuator to selectively displace the movable element from a first position wherein one of said two holders is aligned with the first inlet and outlet so that correspondingly received said particle capturing element captures the particles during a first predetermined period of time, to a second position where said one holder having the selected capturing element received therein is aligned with the secondary aperture so as to be inspected upon operation of the optical sensing device.

2. The apparatus of claim 1, further comprising a capturing element cleaning device provided with a cleaning fluid source connected to a cleaning fluid carrying line in fluid communication with a second inlet defined by another one said main aperture of said second stationary element and a second outlet defined by one corresponding said main aperture of said first stationary element through a corresponding said channel, the cleaning fluid removing said captured particles upon circulation through said channel, at least two of said holders being located on said movable element so as to be simultaneously aligned with said first inlet and said second inlet respectively upon controlled movement of said movable element;

wherein in said first position the other one of said two holders has a previously inspected one element correspondingly received therein and is aligned with the second inlet and outlet so as to be cleaned upon operation of the cleaning device.

3. The apparatus of claim 2, wherein said cleaning fluid source is a forced air source and said cleaning fluid carrying line is an air carrying line.

4. The apparatus of claim 3, wherein said cleaning device is further provided with an exhaust container in communication with said second outlet to receive said removed particles.

5. The apparatus of claim 1, further comprising a frame, said first and second stationary elements are first and second stationary plates secured to the frame to extend in a parallel spaced relationship, said movable element being a movable plate extending in parallel relationship between the first and second stationary plates.

6. The apparatus of claim 5, wherein said first and second stationary plates defines a central axis extending perpendicularly therethrough and around which said main apertures of each said set are symmetrically disposed, said actuator being a rotary actuator being mechanically coupled to said movable plate to impart a rotary movement thereof about the central axis.

7. The apparatus of claim 1, wherein said optical sensing device include an electronic camera and an illumination device directed toward a capturing surface of said selected element, said optical characteristics represented by said signal being reflectance characteristics.

8. An apparatus for estimating the quantity of particles on at least a first surface of a web traveling through a collecting area, comprising:

an air suction extractor including a first particle collecting head having an air intake disposed within the collecting area in close proximity to the first web surface and coupled to an output air carrying line connected to an air suction source to convey collected particles through said output line;

a capturing element handling assembly including first and second stationary elements disposed in a spaced relationship to define a gap therebetween, said stationary elements being provided with respective sets of main apertures disposed in alignment with each other to define a corresponding set of channels extending through the gap, a movable element interposed within the gap and being provided with a plurality of holders capable of receiving a plurality of filter-type particle capturing elements, and an actuator operatively coupled to the movable element for providing controlled movement of the movable element relative to the stationary elements, wherein one said main aperture on the first stationary element defines a first inlet in fluid communication, with the output fluid carrying line and one corresponding said aligned main aperture on the second stationary element defines a first outlet for fluid communication with the output fluid carrying line through a corresponding said channel;

an optical sensing device disposed in alignment with a secondary aperture provided on the first stationary element and extending therethrough to communicate with the gap, for inspecting a selected one of said particle capturing element to generate a measurement signal representative of optical characteristics of the collected particles as captured by the selected element;

a data processor for analyzing the measurement signal to generate an estimation of the quantity of particles captured by the selected element; and a controller operatively connected to the actuator to selectively displace the movable element from a first position wherein one of said two holders is aligned with the first inlet and outlet so that correspondingly received said particle capturing element captures the particles during a first predetermined period of time, to a second position where said one holder having the selected capturing element received therein is aligned with the secondary aperture so as to be inspected upon operation of the optical sensing device.

9. The apparatus of claim 8, further comprising a capturing element cleaning device provided with a cleaning fluid source connected to a cleaning fluid carrying line in fluid communication with a second inlet defined by another one said main aperture of said second stationary element and a second outlet defined by one corresponding said main aperture of said first stationary element through a corresponding said channel, the cleaning fluid removing said captured particles upon circulation through said channel, at least two of said holders being located on said movable element so as to be simultaneously aligned with said first inlet and said second inlet respectively upon controlled movement of the movable element; wherein in said first position the other one of said two holders has a previously inspected one element correspondingly received therein and is aligned with the second inlet and outlet so as to be cleaned upon operation of the cleaning device.

10. The apparatus of claim 9, wherein said cleaning fluid source is a forced air source and said fluid carrying line is an air carrying line.

11. The apparatus of claim 10, wherein said cleaning device is further provided with an exhaust container in communication with said second outlet to receive said removed particles.

12. The apparatus of claim 8, further comprising a frame, said first and second stationary elements are first and second stationary plates secured to the frame to extend in a parallel spaced relationship, said movable element being a movable plate extending in parallel relationship between the first and second stationary plates.

13. The apparatus of claim 12, wherein said first and second stationary plates defines a central axis extending perpendicularly therethrough and around which said main apertures of each said set are symmetrically disposed, said actuator being a rotary actuator being mechanically coupled to said movable plate to impart a rotary movement thereof about the central axis.

14. The apparatus of claim 8, wherein said optical sensing device include an electronic camera and an illumination device directed toward a capturing surface of said selected element, said optical characterisics represented by said signal being reflectance characteristics.

15. The apparatus of claim 8, wherein said first particle collecting head further has an air injector disposed upstream of said air intake in the traveling direction of said web and connected to a forced air source for feeding an air flow toward the air intake to dislodge and convey said particles toward the air intake.

16. The apparatus of claim 8, wherein said air suction extractor further includes:

a second particle collecting head disposed within said collecting area in opposed spaced relationship with said first particle collecting head and having an air intake in close proximity to a second surface of said web opposed to said first web surface, and coupled to said output air carrying line to convey collected particles therethrough; and a valve for selectively coupling said first and second particle collecting head to said air carrying line to allow conveying therethrough particles collected from a selected one of said first and second web surfaces.

17. The apparatus of claim 16, wherein each said particle collecting head has an air injector disposed upstream of said air intake in the traveling direction of said web and connected to a forced air source for creating an air flow toward the air intake to dislodge and convey said particles toward the air intake.

18. A method for estimating the quantity of particles collected by a suction extractor through an output fluid carrying line provided thereon, comprising the steps of:

i) interposing a first filter-type particle capturing element within said output fluid carrying line during a first predetermined period of time to capture a corresponding quantity of said collected particles;

ii) inspecting the particle-capturing element with an optical sensor during a second predetermined period of time to generate a measurement signal representative of optical characteristics of the collected particles as captured by the element:

iii) analyzing the measurement signal to generate an estimation of the quantity of particles captured by the element;

iv) circulating a cleaning fluid through the first particle capturing element in a direction so as to remove said quantity of collected particles; and simultaneously to said step iv):

v) interposing a further filter-type particle capturing element within said output fluid carrying line during a further said first predetermined period of time to capture a corresponding further quantity of said collected particles;

vi) repeating said steps ii) and iii) with the further particle capturing element.

19. The method of claim 18, wherein said steps i) to iii) are repeated after said step iv) with cleaned said first particle capturing element.

20. The method of claim 18, further comprising before said step i), the step of:

a) inspecting said first particle capturing element with said optical sensor to generate a reference signal representative of optical characteristics of a said first particle capturing element substantially free of said particles;

b) analyzing the reference signal to generate a calibrating signal corresponding to a substantially zero quantity of said particles on the first element;

wherein said step iii) includes comparing the measurement signal with the reference signal to generate said estimation of the quantity of particles captured by the element, said steps a) and b) being repeated before said step v) with said further particle capturing element.

21. A method for estimating the quantity of particles on at least a first surface of a web traveling through a collecting area, comprising the steps of:

i) applying suction within the collecting area in close proximity to the first web surface to collect said particles and convey thereof through an output air carrying line;

ii) interposing a first filter-type particle-capturing element within the output fluid carrying line during a predetermined period of time to capture a corresponding quantity of said collected particles;

iii) inspecting the first particle-capturing element with an optical sensor to generate a measurement signal representative of optical characteristics of the collected particles as captured by the element;

iv) analyzing said measurement signal to generate an estimation of the quantity of particles captured by the element;

v) circulating a cleaning fluid through the first particle capturing element in a direction so as to remove said quantity of collected particles; and simultaneously to said step v);

vi) interposing a further filter-type particle capturing element within the output fluid carrying line during a further said predetermined period of time to capture a corresponding further quantity of said collected particles;

vii) repeating said steps iii) and iv) with the further particle capturing element.

22. The method of claim 21, wherein said steps ii) to iv) are repeated after said step v) with cleaned said first particle capturing element.

23. The method of claim 21, further comprising before said step i), the step of:
  a) inspecting said first particle capturing element with said optical sensor to generate a reference signal representative of optical characteristics of the first particle capturing element substantially free of said particles;
  b) analyzing the reference signal to generate a calibrating signal corresponding to a substantially zero quantity of said particles on the first element;
  wherein said step iv) includes comparing said measurement signal with the reference signal to generate said estimation of the quantity of particles captured by said element, said steps a) and b) being repeated before said step vi) with said further particle capturing element.

* * * * *

UNITED STATES PATENT AND TRADEMARK OFFICE
CERTIFICATE OF CORRECTION

PATENT NO. : 6,842,244 B2
DATED : January 11, 2005
INVENTOR(S) : Pierre Bédard et al.

It is certified that error appears in the above-identified patent and that said Letters Patent is hereby corrected as shown below:

Column 1,
Line 40, the term "dogging" should read -- clogging --.

Column 4,
Line 38, the comma following the term "a" should be deleted.

Column 11,
Line 8, the term "LF-114-D-MINI" should read -- LF-1/4-D-MINI --.

Column 12,
Line 38, the numeral -- 10 -- should be after the term "apparatus".

Column 13,
Line 35, the term "staus" should read -- status --.
Line 47, the terms "a shown" should read -- as shown --.

Column 17,
Line 66, the term "45c" should read -- 45 --.

Column 18,
Line 52, the term "said" should be deleted.

Column 20,
Line 44, the numeral -- 11 -- should read "11I".

Signed and Sealed this

Fourth Day of October, 2005

JON W. DUDAS
*Director of the United States Patent and Trademark Office*